US009623146B2

(12) United States Patent
Lamberti et al.

(10) Patent No.: US 9,623,146 B2
(45) Date of Patent: Apr. 18, 2017

(54) BONE IMPLANT MATERIALS COMPRISING CROSS-LINKED BIOACTIVE HYDROGEL MATRICES

(71) Applicant: Pioneer Surgical Technology, Inc., Marquette, MI (US)

(72) Inventors: Francis Vincent Lamberti, Cary, NC (US); Richard Chris Klann, Washington, NC (US); Ronald Stewart Hill, Greenville, NC (US)

(73) Assignee: RTI Surgical Technology, Inc., Marquette, MI (US)

(*) Notice: Subject to any disclaimer, the term of this patent is extended or adjusted under 35 U.S.C. 154(b) by 0 days.

(21) Appl. No.: 14/610,487

(22) Filed: Jan. 30, 2015

(65) Prior Publication Data

US 2015/0140116 A1 May 21, 2015

Related U.S. Application Data

(60) Division of application No. 13/793,644, filed on Mar. 11, 2013, now Pat. No. 8,957,050, which is a continuation of application No. 13/252,500, filed on Oct. 4, 2011, now Pat. No. 8,664,202, which is a division of application No. 12/782,322, filed on May 18, 2010, now Pat. No. 8,053,423, which is a division of application No. 10/372,643, filed on Feb. 21, 2003, now Pat. No. 7,799,767.

(60) Provisional application No. 60/358,625, filed on Feb. 21, 2002.

(51) Int. Cl.

| *A01N 57/16* | (2006.01) |
|---|---|
| *A61L 27/22* | (2006.01) |
| *A61L 27/26* | (2006.01) |
| *A61L 27/34* | (2006.01) |
| *A61L 27/52* | (2006.01) |
| *A61L 31/10* | (2006.01) |
| *A61L 27/02* | (2006.01) |
| *A61L 27/12* | (2006.01) |
| *A61L 27/36* | (2006.01) |
| *A61F 2/00* | (2006.01) |
| *A61K 47/42* | (2017.01) |
| *A61L 27/20* | (2006.01) |
| *A61L 27/24* | (2006.01) |
| *A61L 27/54* | (2006.01) |
| *B29C 39/00* | (2006.01) |
| *B29L 31/00* | (2006.01) |

(52) U.S. Cl.
CPC ......... *A61L 27/222* (2013.01); *A61F 2/0063* (2013.01); *A61K 47/42* (2013.01); *A61L 27/025* (2013.01); *A61L 27/12* (2013.01); *A61L 27/20* (2013.01); *A61L 27/22* (2013.01); *A61L 27/24* (2013.01); *A61L 27/26* (2013.01); *A61L 27/34* (2013.01); *A61L 27/3608* (2013.01); *A61L 27/52* (2013.01); *A61L 27/54* (2013.01); *A61L 31/10* (2013.01); *B29C 39/003* (2013.01); *A61L 2300/112* (2013.01); *A61L 2300/412* (2013.01); *A61L 2430/02* (2013.01); *B29L 2031/7532* (2013.01); *Y10T 428/29* (2015.01); *Y10T 428/2947* (2015.01); *Y10T 428/31551* (2015.04); *Y10T 428/31786* (2015.04)

(58) Field of Classification Search
None
See application file for complete search history.

(56) References Cited

U.S. PATENT DOCUMENTS

| 4,446,316 A | 5/1984 | Chazov et al. |
|---|---|---|
| 4,520,821 A | 6/1985 | Schmidt et al. |
| 4,563,350 A * | 1/1986 | Nathan ............... A61L 27/227 106/124.7 |
| 4,614,794 A | 9/1986 | Easton et al. |

(Continued)

FOREIGN PATENT DOCUMENTS

| EP | 0 213 908 | 3/1987 |
|---|---|---|
| WO | WO 92/19195 | 11/1992 |

(Continued)

OTHER PUBLICATIONS

Anderson, V. and Jones, R., "The Influence of Gelatin on the Mechanism of Phase Separation of a Biopolymer Mixture," *Polymer*, 2001, pp. 9601-9610, vol. 42, Elsevier Science Ltd.

(Continued)

*Primary Examiner* — Hope Robinson
(74) *Attorney, Agent, or Firm* — Womble Carlyle Sandridge & Rice, LLP

(57) ABSTRACT

The present invention is directed to a stabilized cross-linked hydrogel matrix comprising a first high molecular weight component and a second high molecular weight component that are covalently linked, and at least one stabilizing or enhancing agent, wherein the first high molecular weight component and the second high molecular weight component are each selected from the group consisting of polyglycans and polypeptides. This stabilized hydrogel matrix may be prepared as bioactive gels, pastes, slurries, cell attachment scaffolds for implantable medical devices, and casting or binding materials suitable for the construction of medical devices. The intrinsic bioactivity of the hydrogel matrix makes it useful as a gel or paste in multiple applications, including as a cell attachment scaffold that promotes wound healing around an implanted device, as gels and pastes for induction of localized vasculogenesis, wound healing, tissue repair, and regeneration, as a wound adhesive, and for tissue bulking.

8 Claims, 7 Drawing Sheets

(56) References Cited

U.S. PATENT DOCUMENTS

| | | | |
|---|---|---|---|
| 4,618,490 | A | 10/1986 | De Marco |
| 4,772,468 | A | 9/1988 | Pfirrmann |
| 4,863,856 | A | 9/1989 | Dean, Jr. et al. |
| 4,883,487 | A | 11/1989 | Yoshizato et al. |
| 4,895,724 | A | 1/1990 | Cardinal et al. |
| 4,902,295 | A | 2/1990 | Walthall et al. |
| 4,950,483 | A | 8/1990 | Ksander et al. |
| 4,957,902 | A | 9/1990 | Grinnell |
| 4,997,753 | A | 3/1991 | Dean, Jr. et al. |
| 5,099,012 | A | 3/1992 | Wu et al. |
| 5,100,783 | A | 3/1992 | Dean, Jr. et al. |
| 5,263,983 | A | 11/1993 | Yoshizato et al. |
| 5,290,558 | A | 3/1994 | O'Leary et al. |
| 5,303,718 | A | 4/1994 | Krajicek |
| 5,350,583 | A | 9/1994 | Yoshizato et al. |
| 5,376,375 | A | 12/1994 | Rhee et al. |
| 5,457,093 | A | 10/1995 | Cini et al. |
| 5,470,911 | A * | 11/1995 | Rhee .................. C09J 189/06 |
| | | | 525/54.1 |
| 5,484,601 | A | 1/1996 | O'Leary et al. |
| 5,514,379 | A | 5/1996 | Weissleder et al. |
| 5,569,468 | A | 10/1996 | Modi |
| 5,591,709 | A | 1/1997 | Lindenbaum |
| 5,605,938 | A | 2/1997 | Roufa et al. |
| 5,614,205 | A | 3/1997 | Usala |
| 5,645,591 | A | 7/1997 | Kuberasampath et al. |
| 5,705,485 | A | 1/1998 | Cini et al. |
| 5,707,877 | A | 1/1998 | Siiman et al. |
| 5,716,404 | A | 2/1998 | Vacanti et al. |
| 5,718,012 | A | 2/1998 | Cavallaro |
| 5,733,337 | A | 3/1998 | Carr, Jr. et al. |
| 5,756,715 | A | 5/1998 | Monte et al. |
| 5,783,214 | A | 7/1998 | Royer |
| 5,800,541 | A | 9/1998 | Rhee et al. |
| 5,824,331 | A | 10/1998 | Usala |
| 5,830,492 | A | 11/1998 | Usala |
| 5,834,005 | A | 11/1998 | Usala |
| 5,866,165 | A | 2/1999 | Liu et al. |
| 5,922,339 | A | 7/1999 | Usala |
| 5,972,385 | A | 10/1999 | Liu et al. |
| 5,993,844 | A | 11/1999 | Abraham et al. |
| 6,011,008 | A | 1/2000 | Domb et al. |
| 6,077,916 | A | 6/2000 | Laurencin et al. |
| 6,132,759 | A | 10/2000 | Schacht et al. |
| 6,165,488 | A | 12/2000 | Tardy et al. |
| 6,197,330 | B1 | 3/2001 | Rees et al. |
| 6,231,881 | B1 | 5/2001 | Usala et al. |
| 6,261,587 | B1 | 7/2001 | Usala |
| 6,303,585 | B1 | 10/2001 | Spiro et al. |
| 6,352,707 | B1 | 3/2002 | Usala |
| 6,391,052 | B2 | 5/2002 | Buirge et al. |
| 6,458,386 | B1 | 10/2002 | Schacht et al. |
| 6,833,408 | B2 | 12/2004 | Sehl et al. |
| 7,303,814 | B2 | 12/2007 | Lamberti et al. |
| 8,609,122 | B2 | 12/2013 | Lamberti et al. |
| 2002/0019516 | A1 | 2/2002 | Noff et al. |
| 2002/0049281 | A1 | 4/2002 | Zhao et al. |

FOREIGN PATENT DOCUMENTS

| | | |
|---|---|---|
| WO | WO 95/14037 | 5/1995 |
| WO | WO 97/41899 | 11/1997 |
| WO | WO 98/15299 | 4/1998 |
| WO | WO 00/02600 | 1/2000 |
| WO | WO 00/56251 | 9/2000 |
| WO | WO 01/74411 | 10/2001 |

OTHER PUBLICATIONS

Antonov, Y. and Zubova, O., "Phase State of Aqueous Gelatin-Polysaccharide (1)-Polysaccharide (2) Systems," *International Journal of Biological Macromolecules*, 2001, pp. 67-71, vol. 29, Elsevier Science Ltd., B.V.

Arnold, P., et al., "Evaluation of Resorbable Barriers for Preventing Surgical Adhesions," *Fertility and Sterility*, 2000, pp. 157-161, vol. 73(1), Elsevier Science Inc.

Aso, Y., et al., "Thermally Controlled Protein Release From Gelatin-Dextran Hydrogels," *Radiation Physics and Chemistry*, 1999, pp. 179-183, vol. 55, Elsevier Science Ltd.

Ayhan, F., et al., "Optimization of Urease Immobilization onto Non-Porous HEMA Incorporated Poly(EGDMA) Microbeads and Estimation of Kinetic Parameters," *Bioresource Technology*, 2002, pp. 131-140, vol. 81, Elsevier Science Ltd.

Bae, J.S., et al., "Synthesis and Characterization of Harparinized Polyurethanes Using Plasma Glow Discharge," *Biomaterials*, 1999, pp. 529-537, vol. 20(6).

Bailey, A.J. and Light, N.D., "Intermolecular Cross-Linking in Fibrotic Collagen," *Ciba Found Symp.*, 1985, pp. 80-96, vol. 114.

Barié, N., et al., "Covalent Photolinker-Mediated Immobilization of an Intermediate Dextran Layer to Polymer-Coated Surfaces for Biosensing Applications," *Biosensors & Bioelectronics*, 1998, pp. 855-860, vol. 13, Elsevier Science S.A.

Barker, H., et al., "Formaldehyde as a Pre-Treatment of Dermal Collagen Heterografts," *Biochimica et Biophysica Acta*, 1980, pp. 589-597, vol. 632.

Ben Slimane, S., et al., Characteristics of Polyester Arterial Grafts Coated with Albumin, the Role and the Importance of the Crosslinking Chemicals, *Eur. Surg. Res.*, 1988, pp. 18-28, vol. 20.

Bisson, I., et al., "Acrylic Acid Grafting and Collagen Immobilization on Poly(ethylene terephthalate) Surfaces for Adherence and Growth of Human Bladder and Smooth Muscle Cells," *Biomaterials*, 2002, pp. 3149-3158, vol. 23, Elsevier Science Ltd.

Bos, G.W., et al., "Proliferation of Endothelial Cells on Surface-Immobilized Albumin-Heparin Conjugate Loaded with Basic Fibroblast Growth Factor," *J. Biomed. Mater. Res.*, 1999, pp. 330-340, vol. 44, John Wiley & Sons, Inc.

Boyan, B.D. et al., "Role of Material Surfaces in Regulating Bone and Cartilage Cell Response," *Biomaterials*, 1996, pp. 137-146, vol. 17.

Boyce, S.T. and Hansborough, J.F., Biologic Attachment, Growth, and Differentiation of Cultured Human Epidermal Keratinocytes on a Graftable Collagen and chondroitin-6-sulfate substrate, *Surgery*, 1988, pp. 421-431, vol. 103.

Bubnis, W.A. and Ofner C.M. III, "The Determination of ∈-Amino Groups in Soluble and Poorly Soluble Proteinaceous Materials by a Spectrophotometric Method Using Trinitrobezenesulfonic Acid," *Anal. Biochem.*, 1992, pp. 129-133, vol. 207.

Bulgarelli, E., et al.,"Casein/Gelatin Beads: I. Cross-Linker Solution Composition Effect on Cross-Linking Degree," 1999, *Int. J. Pharm.*, 1999, pp. 175-182, vol. 190(2).

Butler, C., et al., "Regeneration of Neomucosa Using Cell-Seeded Collagen-GAG Matrices in Athymic Mice," *Annals of Plastic Surgery*, 2002, pp. 298-304, vol. 48, Lippincott Williams & Wilkins, Inc.

Calero, P., et al., "Gelatinases in Soft Tissue Biomaterials. Analysis of Different Crosslinking Agents," *Biomaterials*, 2002, pp. 3473-3478, vol. 23, Elsevier Science Ltd.

Cao, X. and Shoichet, M., "Photoimmobilization of Biomolecules within a 3-Dimensional Hydrogel Matrix," *J. Biomater. Sci. Polymer Edn.*, 2002, pp. 623-636, vol. 13(6).

Chandy, T., et al., "Use of Plasma Glow for Surface-Engineering Biomolecules to Enhance Bloodcompatibility of Dacron and PTFE Vascular Prosthesis," *Biomaterials*, 2000, pp. 699-712, vol. 21, Elsevier Science Ltd.

Charulatha, V. and Rajaram, A., "Crosslinking Density and Resorption of Dimethyl Suberimimidate-Treated Collagen," *J. Biomed. Mater. Res.* 1997, pp. 478-486, vol. 15.

Charulatha, V. and Rajaram, A., "Dimethyl 3,3'-dithiobispropionimidate: A Novel Crosslinking Reagent for Collagen," *J. Biomed. Mater. Res.*, 2001, pp. 122-128, vol. 54.

Chegel, V., et al., "A Novel Aldehyde Dextran Sulfonate Matrix for Affinity Biosensors," *J. Biochem. Biophys. Methods*, 2002, pp. 201-216, vol. 50, Elsevier Science B.V.

Chen, T., et al., "In Vitro Protein-Polysaccharide Conjugation: Tyrosinase-Catalyzed Conjugation of Gelatin and Chitosan," *Biopolymers*, 2002, pp. 292-302, vol. 64, Wiley Periodicals, Inc.

(56) References Cited

OTHER PUBLICATIONS

Chevolot, Y., et al., "Immobilisation on Polystyrene of Diazirine Derivatives of Mono-and Disaccharides: Biological Activities of Modified Surfaces," *Bioorganic & Medicinal Chemistry*, 2001, pp. 2943-2953, vol. 9, Elsevier Science Ltd.

Choi, Y., et al., "Study on Gelatin-Containing Artificial Skin: I. Preparation and Characteristics of Novel Gelatin-Alginate Sponge," *Biomaterials*, 1999, pp. 409-417, vol. 20, Elsevier Science Ltd.

Choi, Y., et al., "Studies on Gelatin-Containing Artificial Skin: II. Preparation and Characterization of Cross-Linked Gelatin-Hyaluronate Sponge," *J. Biomed. Mater. Res. (Appl. Biomater.)* 1999, pp. 631-639, vol. 48, John Wiley & Sons, Inc.

Chowdhury, D.K. and Mitra, A. K., "Kinetics of In Vitro Release of a Model Nucleoside Deoxyruridine from Crosslinked Insoluble Collagen and Collagen-Gelatin Microspheres," *International Journal of Pharmaceutics*, 1999, pp. 113-122, vol. 193.

Chu, P., et al., "Plasma-Surface Modification of Biomaterials," *Materials Science and Engineering R*, 2002, pp. 143-206, vol. 36, Elsevier Science B.V.

Clods, P. and Christgau, S., "Non-Enzymatic Covalent Modifications of Proteins: Mechanisms, Physiological Consequences and Clinical Applications," *Matrix Biology*, 2002, pp. 39-52, vol. 21, Elsevier Science B.V.

Cortesi, R., et al., "Dextran Cross-Linked Gelatin Microspheres as a Drug Delivery System," *Eur. J. Pharm. Biopharm.*, 1999, pp. 153-160, vol. 47.

Cortesi, R., et al., "Sugar Cross-Linked Gelatin for Controlled Release: Microspheres and Disks," *Biomaterials*, 1998, pp. 1641-1649, vol. 19, Elsevier Science Ltd.

Crescenzi, V., et al., "New Gelatin-Based Hydrogels Via Enzymatic Networking," *Biomacromolecules*, 2002, pp. 1384-1391, vol. 3, American Chemical Society.

Dai, L., et al., "Biomedical Coatings by the Covalent Immobilization of Polysaccharides onto Gas-Plasma-Activated Polymer Surfaces," *Surface and Interface Analysis*, 2000, pp. 46-55, vol. 29, John Wiley & Sons, Ltd.

Dean et al., "Chapter 1. Matrix Preparations and Applications," in *Affinity Chromatophraphy: A Practical Approach*, 1985, IRL Press.

Dean et al., "Chapter 2. Activation Procedures," in *Affinity Chromatophraphy: A Practical Approach*, 1985, IRL Press.

Dean et al., "Chapter 3. Cross-Linking Agents for Coupling Matrices to Spacers," in *Affinity Chromatophraphy: A Practical Approach*, 1985, IRL Press.

De Kruif, C. and Tuinier, R., "Polysaccharide Protein Interactions," *Food Hydrocolloids*, 2001, pp. 555-563, vol. 15, Elsevier Science Ltd.

Denuziere, A., et al., "Chitosan-Chondroitin Sulfate and Chitosan-Hyaluronate Polyelectrolyte Complexes: Biological Properties," *Biomaterials*, 1998, pp. 1275-1285, vol. 19, Elsevier Science Ltd.

Denuziere, A., et al., "Chitosan-Chondroitin Sulfate and Chitosan-Hyaluronate Polyelectrolyte Complexes: Physico-Chemical Aspects," *Carbohydrate Polymers*, 1996, pp. 317-323, vol. 29.

Ding, P., et al., "Interfacial Tension in Phase-Separated Gelatin/Dextran Aqueous Mixtures," *Journal of Colloid and Interface Science*, 2002, pp. 367-376, vol. 253, Elsevier Science USA.

Doukas, J., et al., "Delivery of FGF Genes to Wound Repair Cells Enhances Arteriogenesis and Myogenesis in Skeletal Muscle," *Molecular Therapy*, 2002, pp. 517-527, vol. 5(5), The American Society of Gene Therapy.

Draye, J.P., et al., "In vitro Release Characteristics of Bioactive Molecules from Dextran Dialdehyde Cross-Linked Gelatin Hydrogel Films," *Biomaterials*, 1998, pp. 99-107, vol. 19, Elsevier Science Ltd.

Draye, J.P., et al., "In vitro and in vivo Biocompatibility of Dextran Dialdehyde Cross-Linked Gelatin Hydrogel Films," *Biomaterials*, 1998, pp. 1677-1687, vol. 19, Elsevier Science Ltd.

Drury et al., "Hydrogels for Tissue Engineering: Scaffold Design Variables and Applications," *Biomaterials*, 2003, pp. 4337-4351, vol. 24.

Dumitriu, S. and Chornet, E., "Inclusion and Release of Proteins from Polysaccharide-Based Polyion Complexes," *Advanced Drug Delivery Reviews*, 1998, pp. 223-246, vol. 31.

Duncan, A., et al., "Preparation and Characterization of a Poly (2-hydroxyethyl methacrylate) Biomedical Hydrogel," *European Polymer Journal*, 2001, pp. 1821-1826, vol. 37, Elsevier Science Ltd.

Eckert, A., et al., "Surface-Modification of Polystyrene-Microtitre Plates Via Grafting of Glycidylmethacrylate and Coating of Poly-Glycidylmethacrylate," *Biomaterials*, 2000, pp. 441-447, vol. 21, Elsevier Science Ltd.

Edelman, M. and Van Der Linden, E., "Compatability of Gelatin and Dextran in Aqueous Solution," *Biomacromolecules*, 2001, pp. 1148-1154, vol. 2(4), American Chemical Society.

Edwards, G., et al., "In vivo Evaluation of a Collagenous Membrane as an Absorbable Adhesion Barrier," *Journal of Biomedical Materials Research*, 1997, pp. 291-297, vol. 34, John Wiley & Sons, Inc.

Einerson, N., et al., "Synthesis and Physiochemical Analysis of Gelatin-Based Hydrogels for Drug Carrier Matrices," *Biomaterials*, 2002, pp. 509-523, vol. 24, Elsevier Science Ltd.

Englebretsen, D.R. and Harding D.R., "High Yield, Directed Immobilization of a Peptide-Ligand onto a Beaded Cellulose Support," 1994, *Peptide Research*, pp. 322-326, vol. 7(6).

Esposito, E., et al., "Gelatin Microspheres: Influence of Preparation Parameters and Thermal Treatment on Chemico-Physical and Biopharmaceutical Properties," *Biomaterials*, 1996, pp. 2009-2020, vol. 17(20), Elsevier Science Limited, Great Britain.

Fan, H. and Dash, A.K., "Effect of Cross-Linking on the in vitro Release Kinetics of Doxorubicin from Gelatin Implants," *Int. J. Pharma.*, 2001, pp. 103-116, vol. 213.

Franssen, O. and Hennink, W., "A Novel Preparation Method for Polymeric Microparticles without the Use of Organic Solvents," *Int. J. Pharma.*, 1998, pp. 1-7, vol. 168, Elsevier Science B.V.

Freyman, T., et al., "Fibroblast Contraction of a Collagen-GAG Matrix," *Biomaterials*, 2001, pp. 2883-2891, vol. 22.

Freyman, T., et al., "Micromechanics of Fibroblast Contraction of a Collagen-GAG Matrix," *Experimental Cell Research*, 2001, pp. 140-153, vol. 269, Academic Press.

Friess, W., et al., "Insoluble Collagen Matrices for Prolonged Delivery of Proteins," *Pharm Dev. Technol.*, 1996, pp. 185-193, vol. 1(2).

Fujimori, E., "Cross-Linking and Fluorescence Changes of Collagen by Glycation and Oxidation," *Biochim Biophys Acta*, 1989, pp. 105-110, vol. 998.

Gekko, K. and Fukamizu, M., "Effect of Pressure on the Sol-Gel Transition of Gelatin," *Int. J. Biol. Macromol.*, 1991, pp. 295-300, vol. 13.

Gérentes, P., et al., "Study of a Chitin-Based Gel as Injectable Material in Periodontal Surgery," *Biomaterials*, 2002, pp. 1295-1302, vol. 23, Elsevier Science Ltd.

Gregorius, K. and Theisen, M., "In Situ Deprotection: A Method for Covalent Immobilization of Peptides with Well-Defined Orientation for Use in Solid Phase Immunoassays Such As Enzyme-Linked Immunosorbent Assay," *Analytical Biochemistry*, 2001, pp. 84-91, vol. 299, Academic Press.

Griffon, D., "Evaluation of Osteoproductive Biomaterials: Allograft, Bone Inducing Agent, Bioactive Glass, and Ceramics," Academic Dissertation, Sep. 6, 2002, Dept. of Clinical Veterinary Sciences, University of Helsinki, Finland.

Hansbrough, J.F., et al., "Burn Wound Closure with Cultured Autologous Keratinocytes and Fibroblasts Attached to a Collagen-Glycoasminoglycan Substrate," *JAMA*, 1989, pp. 2125-2130, vol. 262.

Harding, J. J., "The Unusual Links and Cross-Links of Collagen," *Adv. Protein Chem.*, 1965, pp. 109-190, vol. 20.

Heath, D., et al., "Involvement of Tissue Transglutaminase in the Stabilisation of Biomaterial/Tissue Interfaces Important in Medical Devices," *Biomaterials*, 2002, pp. 1519-1526, vol. 23, Elsevier Science Ltd.

Heiduschka, P. and Thanos, S., "Implantable Bioelectronic Interfaces for Lost Nerve Functions," *Progress in Neurobiology*, 1998, pp. 433-461, vol. 55.

(56) References Cited

OTHER PUBLICATIONS

Heijmen, F.H., et al., "Cross-Linking of Dermal Sheep Collagen with Tannic Acid," *Biomaterials*, 1997, pp. 749-754, vol. 18.
Holmes, T., "Novel Peptide-Based Biomaterial Scaffolds for Tissue Engineering," *TRENDS in Biotechnology*, 2002, pp. 16-21, vol. 20 (1), Elsevier Science, Ltd.
Hoffman, "Hydrogels for Biomedical Applications," *Advanced Drug Delivery Reviews*, 2012, doi: 10.1016/j.addr.2012.09.010.
Hong, S., et al., "Study on Gelatin-Containing Artificial Skin IV: A Comparative Study on the Effect of Antibiotic and EGF on Cell Proliferation During Epidermal Healing," *Biomaterials*, 2001, pp. 2777-2783, vol. 22, Elsevier Science Ltd., United Kingdom.
Hörmann, H. et al., "Immobilization of Soluble Fibrin on Fact or XIIa-Coated Polystyrene Beads Mediated by N-Terminal Fibronectin Fragments. II. Demonstration of Covalent Adducts of Fibrin Peptide Chains and Fibronectin Fragments," *Biol. Chem. Hoppe Seyler*, 1991, pp. 427-430, vol. 372.
Huh, K., et al., "Synthesis and Characterization of Dextran Grafted with Poly(N-isopropylacrylamide-co-N,N-dimethyl-acrylamide)," *Macromol. Chem. Phys.*, 2000, pp. 613-619, vol. 201.
Hutmacher, D., "Scaffolds in Tissue Engineering Bone and Cartilage," *Biomaterials*, 2000, pp. 2529-2543, vol. 21, Elsevier Science Ltd.
Iooss, P., et al., "A New Injectable Bone Substitute Combining poly(ε-caprolactone) Microparticles with Biphasic Calcium Phosphate Granules," *Biomaterials*, 2001, pp. 2785-2794, vol. 22, Elsevier Science Ltd.
Isgrove, F., et al., "Enzyme Immobilization on Nylon-Optimization and the Steps Used to Prevent Enzyme Leakage from the Support," *Enzyme and Microbial Technology*, 2001, pp. 225-232, vol. 28, Elsevier Science Inc.
Ito, Y., "Micropattern Immobilization of Polysaccharide," *Journal of Inorganic Biochemistry*, 2000, pp. 77-81, vol. 79, Elsevier Science Inc.
Ito, Y., et al., "Artificial Juxtacrine Stimulation for Tissue Engineering," *J. Biomater. Sci. Polymer Edn*, 1998, pp. 879-889, vol. 9(8).
Jansson, K., et al., "A Biodegradable Collagen Membrane as a Dermal Template for Human in vivo Wound Healing," *Scand. J. Plast. Reconstr. Hand Surg.*, 2001, pp. 369-375, vol. 35.
Johnson, R.E., et al., "Thermodynamics of Protein Cross-Links," *Biochemistry*, 1978, pp. 1479-1484, vol. 17(8).
Kaeselev, B., et al., "Photoinduced Grafting of Ultrafiltration Membranes: Comparison of poly(ether sulfone) and poly(sulfone)," *Journal of Membrane Science*, 2001, pp. 245-261, vol. 194, Elsevier Science B.V.
Kam, L., et al., "Selective Adhesion of Astrocytes to Surfaces Modified with Immobilized Peptides," *Biomaterials*, 2002, pp. 511-515, vol. 23, Elsevier Science Ltd.
Kao, W. and Lee, D., "In vivo Modulation of Host Response and Macrophage Behavior by Polymer Networks Grafted with Fibronectin-Derived Biomimetic Oligopeptides: the Role RGD and PHSRN Domains," *Biomaterials*, 2001, pp. 2901-2909, vol. 22, Elsevier Science Ltd.
Kao, W., et al., "Preparation of Heterodifunctional Polyethyleneglycols: Network Formation, Characterization, and Cell Culture Analysis," *J. Biomater. Sci. Polymer Edn*, 2001, pp. 599-611, vol. 12.
Kawai, K., et al., "Accelerated Tissue Regeneration through Incorporation of Basic Fibroblast Growth Factor-Impregnated Gelatin Microspheres into Artificial Dermis," *Biomaterials*, 2000, pp. 489-499, vol. 21, Elsevier Science Ltd.
Kim, C.J. and Lee, P.I., "Composite poly (vinyl alcohol) Beads for Controlled Drug Delivery," *Pharm. Res.*, 1992, pp. 10-16, vol. 9(1).
Kim, Y.J., et al., "Surface Characterization and in vitro Blood Compatibility of poly(ethylene terephthalate) Immobilized with Insulin and/or Heparin Using Plasma Glow Discharge," *Biomaterials*, 2000, pp. 121-130, vol. 21.
König, U., et al, "Durable Surface Modification of poly(tetrafluoroethylene) by Low Pressure $H_2O$ Plasma Treatment Followed by Acrylic Acid Graft Polymerization," *Colloids and Surfaces B: Biointerfaces*, 2002, pp. 63-71, vol. 24, Elsevier Science B.V.
Koob, T. and Hernandez, D., Material Properties of Polymerized NDGA-Collagen Composite Fibers: Development of Biologically Based Tendon Constructs, *Biomaterials*, 2002, pp. 203-212, vol. 23, Elsevier Science Ltd.
Korrt, A., et al., "Nonspecific Amine Immobilization of Ligand Can Be a Potential Source of Error in BIAcore Binding Experiments and May Reduce Binding Affinities," *Anal. Biochem.*, 1997, pp. 103-111, vol. 253.
Kosmala, J., et al., "Preparation of Interpenetrating Networks of Gelatin and Dextran as Degradable Biomaterials," *Biomaterials*, 2000, pp. 2019-2023, vol. 21, Elsevier Science Ltd.
Kröger, D., et al., "Immobilization of Histidine-Tagged Proteins on Gold Surfaces Using Chelator Thioalkanes," *Biosens. Bioelectron.*, 1999, pp. 155-161, vol. 14.
Kuijpers, A.J., et al., "Controlled Delivery of Antibacterial Proteins from Biodegradable Matrices," *J. Control Release*, 1998, pp. 235-247, vol. 53.
Kuijpers, A.J., et al., "Cross-Linking and Characterizations of Gelatin Matrices for Biomedical Applications," *J. Biomater Sci Polym Ed.*, 2000, pp. 225-243, vol. 11.
Kuijpers, A.J., et al., "In vitro and in vivo Evaluation of Gelatin-Chondroitin Sulphate Hydrogels for Controlled Release of Antibacterial Proteins," *Biomaterials*, 2000, pp. 1763-1772, vol. 21.
Kuijpers, A.J., et al., In vivo and in vitro Release of Lysozyme from Cross-Linked Gelatin Hydrogels: A Model System for the Delivery of Antibacterial Proteins from Prosthetic Heart Valves, *J. Control Release*, 2000, pp. 323-336, vol. 67.
Kuijpers, A.J., et al., "In vivo Compatability and Degradation of Crosslinked Gelatin Gels Incorporated in Knitted Dacron," *J. Biomed Mater Res.*, 2000, pp. 136-145, vol. 51.
Kurisawa, M. and Yui, N., "Gelatin/Dextran Intelligent Hydrogels for Drug Delivery: Dual-Stimuli-Responsive Degradation in Relation to Miscibility in Interpenetrating Polymer Networks," *Macromol. Chem. Phys.*, 1998, pp. 1547-1554, vol. 199, Wiley-VCH Verlag GmbH, D-69451, Weinheim.
Kuzuya, M., et al., "Glycation Cross-Links Inhibit Matrix Metalloproteinase-2 Activation in Vascular Smooth Muscle Cells Cultured on Collagen Lattice," *Diabetologia*, 2001, pp. 433-436, vol. 44.
Lando, D.Y., Melting of Cross-Linked DNA: I. Model and Theoretical Methods, *J. Biomol. Struct. Dyn.*, 1997, pp. 129-140, vol. 15(1).
Larm, O., et al., "A New Non-Thrombogenic Surface Prepared by Selective Covalent Binding of Heparin via a Modified Reducing Terminal Residue," *Biomat. Med. Dev. Artif. Organs*, 1983, pp. 161-173, vol. 11.
Lebaron, R.G., et al., "Extracellular Matrix Cell Adhesion Peptides: Functional Applications in Orthopedic Materials," *Tissue Eng.*, 2000, pp. 85-103, vol. 6(2).
Lee, J.M., et al., "Crosslinking of Tissue-Derived Biomaterials in 1-ethyl-3(3-dimethylaminopropyl)-carbodiimide (EDC)," *J. Mater. Sci. Mat. Med.*, 1996, pp. 531-541, vol. 7.
Lii, C., et al., "Carboxymethyl Cellulose-Gelatin Complexes," *Carbohydrate Polymers*, 2002, pp. 19-26, vol. 50, Elsevier Science Ltd.
Lii, C., et al., "Xanthan Gum-Gelatin Complexes," *European Polymer Journal*, 2002, pp. 1377-1381, vol. 38, Elsevier Science Ltd.
Lin, F., et al., "Biological Effects and Cytotoxicity of the Composite Composed by Tricalcium Phosphate and Glutaraldehyde Cross-Linked Gelatin," *Biomaterials*, 1998, pp. 905-917, vol. 19, Elsevier Science Ltd.
Liu, H., et al., "Osteogenic Evaluation of Glutaraldehyde Crosslinked Gelatin Composite with Fetal Rat Calvarial Culture Model," *Artificial Organs*, 2001, pp. 644-654, vol. 25(8), Blackwell Science, Inc.
Liu, L., et al., "An Osteoconductive Collagen/Hyaluronate Matrix for Bone Regeneration," *Biomaterials*, 1999, pp. 1097-1108, vol. 20, Elsevier Science Ltd.

(56) References Cited

OTHER PUBLICATIONS

Ljungquist, C., et al., "Thiol-Directed Immobilization of Recombinant IgG-Binding Receptors," *Eur. J. Biochem.*, 1989, pp. 557-561, vol. 186.

Lou, X. and Chirila, T.V., "Swelling Behavior and Mechanical Properties of Chemically Cross-Linked Gelatin Gels for Biomedical Use," *J. Biomater. Appl.*, 1999, pp. 184-91, vol. 14(2).

Ma, X., et al., "Thermal Cross-Linking for Biologically Degradable Materials," *ASAIO J.*, Preliminary Report, 1996, pp. M866-M871, vol. 42(5).

Madhan, B., et al., "Study on the Stabilization of Collagen with Vegetable Tannins in the Presence of Acrylic Polymer," *Biomaterials*, 2002, pp. 2841-2847, vol. 23(14).

Marois, Y., et al., "Carbomiimide Cross-Linked Gelatin: A New Coating for Porous Polyester Arterial Prostheses," *Biomaterials*, 1995, pp. 1131-1139, vol. 16.

Massia, S. and Hubbell, J., "Covalent Surface Immobilization of Arg-Gly-Asp- and Tyr-Ile-Gly-Ser-Arg-Containing Peptides to Obtain Well-Defined Cell-Adhesive Substrates," *Analytical Biochemistry*, 1990, pp. 292-301, vol. 187, Academic Press, Inc.

Massia, S. and Stark, J., "Immobilized RGD Peptides on Surface-Grafted Dextran Promote Biospecific Cell Attachment," *J. Biomed. Mater. Res.*, 2001, pp. 390-399, vol. 56, John Wiley & Sons, Inc.

Massia, S., et al., "Surface-Immobilized Dextran Limits Cell Adhesion and Spreading," *Biomaterials*, 2000, pp. 2253-2261, vol. 21, Elsevier Science Ltd.

Matsuda, T. and Magoshi, T., "Preparation of Vinylated Polysaccharides and Photofabrication of Tubular Scaffolds as Potential Use in Tissue Engineering," *Biomacromolecules*, 2002, pp. 942-950, vol. 3, American Chemical Society.

Mentink, C., et al., "Glucose-Mediated Cross-Linking of Collagen in Rat Tendon and Skin," *Clinica Chimica Acta*, 2002, pp. 69-76, vol. 321, Elsevier Science B.V.

Mo, X., et al., "Soft Tissue Adhesive Composed of Modified Gelatin and Polysaccharides," *J. Biomater. Sci. Polymer Edn.*, 2000, pp. 341-351, vol. 11(4), VSP 2000.

Murray, F. and Hutton, P., "Gelling of Urea-Linked Gelatin with Fresh Frozen Plasma," *Anaesthesia*, 1989, pp. 392-393, vol. 44(5).

Naftalin, R.J. and Symonds, M.C., "The Mechanisms of Sugar-Dependent Stabilisation of Gelatin Gels," *Biochim. Biophys. Acta*, 1974, pp. 173-178, vol. 352.

Navarro, F., et al., "Sprayed Keratinocyte Suspensions Accelerate Epidermal Coverage in a Porcine Microwound Model," *J. Burn Care Rehabil.*, 2000, pp. 513-518, vol. 21.

Nguyen, Q., et al., "Simple Method for Immobilization of Bio-Macromolecules onto Membranes of Different Types," *Journal of Membrane Science*, 2002, pp. 1-11, vol. 5494, Elsevier Science B.V.

Nouaimi, M., et al., "Immobilization of Trypsin on Polyester Fleece via Different Spacers," *Enzyme and Microbial Technology*, 2001, pp. 567-574, vol. 29.

Nouvel, C., et al., "Partial or Total Silylation of Dextran with Hexamethyldislazane," *Polymer*, 2002, pp. 1735-1743, vol. 43, Elsevier Science Ltd.

Olbrich, K., et al., "Surfaces Modified with Covalently-Immobilized Adhesive Peptides Affect Fibroblast Population Motility," *Biomaterials*, 1996, pp. 759-764, vol. 17, Elsevier Science Limited.

Olde Damink, L., et al., "Crosslinking of Dermal Sheep Collagen Using Hexamethylene Diisocyanate," *J. Mater. Sci. Mat. Med.*, 1995, pp. 429-434, vol. 6.

Olde Damink, L., et al., "Cross-Linking of Dermal Sheep Collagen Using a Water Soluble Carbodiimide," *Biomaterials*, 1996, pp. 765-773, vol. 17(8).

Olde Damink, L., et al., "Glutaraldehyde as a Crosslinking Agent for Collagen-Based Biomaterials," *J. Mater. Sci. Mat. Med.*, 1995, pp. 460-472, vol. 6.

Otani, Y. et al., Effect of Additives on Gelation and Tissue Adhesion of Gelatin-poly(L-glutamic acid) Mixture, *Biomaterials*, 1998, pp. 2167-2173, vol. 19.

Park, S., et al., "Characterization of Porous Collagen/Hyaluronic Acid Scaffold Modified by 1-ethyl-3-(3-dimethylaminopropyl)carbodiimide Cross-Linking," *Biomaterials*, 2002, pp. 1205-1212, vol. 23, Elsevier Science Ltd.

Pierce Technical Handbook, 1994, Pierce Biotechnology, Inc. (available on-line@www.piercenet.com).

Piez, K.A., "Chemistry of Collagen and Its Cross-Links," *Isr. J. Med. Sci.*, 1971, p. 453, vol. 7(3).

Puleo, D.A., et al., "A Technique to Immobilize Bioactive Proteins, Including Bone Morphogenetic Protein-4 (BMP-4), on Titanium Alloy," *Biomaterials*, 2002, pp. 2079-2087, vol. 23, Elsevier Science Ltd.

Rao, J.K., et al., "Controlled Release Systems for Proteins Based on Gelatin Microspheres," *J. Biomater. Sci, Polym. Ed.*, 1994, pp. 391-398, 1994, vol. 6(5).

Ratner, B., "Reducing Capsular Thickness and Enhancing Angiogenesis Around Implant Drug Release Systems," *J. Control. Release*, 2002, pp. 211-218, vol. 78, Elsevier Science B.V.

Ravin, A., et al., "Long-and Short-Term Effects of Biological Hydrogels on Capsule Microvascular Density Around Implants in Rats," *Journal of Biomedical Material Resources (Applied Biomaterials)*, 2001, pp. 313-318, vol. 58, John Wiley & Sons, Inc.

Rosa, C., et al., "Optical Biosensor Based on Nitrite Reductase Immobilized in Controlled Pore Glass," *Biosen Bioelec.*, 2002, pp. 45-52, vol. 17.

Ruys, L., et al., "Polymer Drug Combinations. VII. Polymethacrylates and Modified Polysaccharides with Potential Antiarrhythmic Activity," *Acta Pharmaceutica Technologica*, 1983, pp. 105-112, vol. 29(2).

Sajithlal, G., et al., "Advanced Glycation End Products Induce Crosslinking of Collagen in vitro," *Biochimica et Biophysica Acta*, 1998, pp. 215-224, vol. 1407, Elsevier Science B.V.

Sakiyama, S.E., et al., "Incorporation of Heparin-Binding Peptides into Fibrin Gels Enhances Neurite Extension: An Example of Designer Matrices in Tissue Engineering," *FASEB J.*, 1999, pp. 2214-2224, vol. 13(15).

Schacht, E., et al., "Hydrogels Prepared by Crosslinking of Gelatin with Dextran Dialdehyde," *Reactive & Functional Polymers*, 1997, pp. 109-116, vol. 33, Elsevier Science B.V.

Scholten, E., et al., "Interfacial Tension of a Decomposed Biopolymer Mixture," *Langmuir*, 2002, pp. 2234-2238, vol. 18(6), American Chemical Society.

Sershen, S. and West, J., "Implantable, Polymeric Systems for Modulated Drug Delivery," *Advanced Drug Delivery Reviews*, 2002, pp. 1225-1235, vol. 54, Elsevier Science B.V.

Shpigel, E., et al., "Immobilization of Recombinant Herparinase I Fused to Cellulose-Binding Domain," *Biotechnol Bioeng.*, Oct. 5, 1999, pp. 17-23, vol. 65(1).

Smeds, K. and Grinstaff, M., "Photocrosslinkable Polysaccharides for In Situ Hydrogel Formation," *J. Biomed. Mater. Res.*, 2001, pp. 115-121, vol. 54, John Wiley & Sons, Inc.

Speer, D.P. et al., "Biological Effects of Residual Glutaraldehyde in Glutaraldehyde-Tanned Collagen," *J. Biomed. Mater. Res.*, 1980, pp. 753-764, vol. 14.

Strauss, A. and Gotz, F., "In vivo Immobilization of Enzymatically Active Polypeptides on the Cell Surface of Staphylococcus Carnosus," *Mol. Microbial.*, 1996, pp. 491-500, vol. 21(3).

Sundholm, F. and Visapaa, A., "Cross-Linking of Collagen in the Presence of Oxidizing Lipid," *Lipids*, 1978, pp. 755-757, vol. 13(11).

Sung, H.W., et al., Crosslinking Characteristics of Biological Tissues Fixed with Monofunctional or Multifunctional Epoxy Compounds, *Biomaterials*, 1996, pp. 1405-1410, vol. 17.

Sutherland, I.W., "Novel and Established Applications of Microbial Polysaccharides," *TIBTECH*, 1998, pp. 41-46, vol. 16.

Tabata, Y, and Ikada, Y., "Vascularization Effect of Basic Fibroblast Growth Factor Released from Gelatin Hydrogels with Different Biodegradabilities," *Biomaterials*, 1999, pp. 2169-2175, vol. 20, Elsevier Science Ltd.

Tromp, R., et al., "Confocal Scanning Light Microscopy (CSLM) on Mixtures of Gelatin and Polysaccharides," *Food Research International*, 2001, pp. 931-938, vol. 34, Elsevier Science Ltd.

Tsai, C., et al., "Effects of Heparin Immobilization on the Surface Characteristics of a Biological Tissue Fixed with a Naturally

(56) References Cited

OTHER PUBLICATIONS

Occurring Crosslinking Agent (Genipin): An in vitro Study," *Biomaterials*, 2001, pp. 523-533, vol. 22, Elsevier Science Ltd.

Ulubayram, K., et al., "EGF Containing Gelatin-Based Wound Dressings," *Biomaterials*, 2001, pp. 1345-1356, vol. 22.

Vandelli, M.A., et al., "The Concentration of the Cross-Linking Agent as a Tool for the Control of Release and Swelling Properties of Gelatin Microspheres," *J. Pharm. Belg.*, 1991, pp. 381-388, vol. 46.

Vandelli, M.A., et al., "The Effect of the Cross-Linking Time Period Upon the Drug Release and the Dynamic Swelling of Gelatin Microspheres," *Pharmazie*, 1991, pp. 866-869, vol. 46(12).

Van Wachem, P., et al., "(Electron) Microscopic Observations on Tissue Integration of Collagen-Immobilized Polyurethane," *Biomaterials*, 2002, pp. 1401-1409, vol. 23, Elsevier Science Ltd.

Van Wachem, P., et al., "In vivo Biocompatibility of Carbodiimide-Crosslinked Collagen Matrices: Effects of Crosslink Density, Heparin Immobilization, and bFGF Loading," *J. Biomed. Mater. Res.*, 2001, pp. 368-378, vol. 55(3).

Vaz, C., et al., "Use of Coupling Agents to Enhance the Interfacial Interactions in Starch-EVOH/Hydroxylapatite Composites," *Biomaterials*, 2002, pp. 629-635, vol. 23, Elsevier Science Ltd.

Walton, D., et al., "Electrosynthetic Modification of Proteins: Electrooxidations at Methionine and Tryptophan in Hen Egg-White Lysozyme," *Electrochimica Acta*, 1997, pp. 2285-2294, vol. 42(15), Elsevier Science Ltd., Great Britain.

Wang, J., et al., "One-Step Electropolymeric Co-Immobilization of Glucose Oxidase and Heparin for Amperometric Biosensing of Glucose," *Analyst*, 2000, pp. 1431-1434, vol. 125.

Weadock, K., et al., "Evaluation of Collagen Crosslinking Techniques," *Biomat. Med. Dev. Art Org.*, 1983, pp. 293-318, vol. 11.

Wells, *Biochemistry*, 1990, pp. 8509-8517, vol. 29.

Welz, M.M. and Ofner, C.M., "Examination of Self-Crosslinked Gelatin as a Hydrogel for Controlled Release," *J. Pharm. Sci.*, 1992, pp. 85-90, vol. 81(1).

Wissink, M., et al., "Binding and Release of Basic Fibroblast Growth Factor from Heparinized Collagen Matrices," *Biomaterials*, 2001, pp. 2291-2299, vol. 22, Elsevier Science Ltd.

Wissink, M., et al., "Immobilization of Heparin to EDC/NHS-Crosslinked Collagen. Characterization and in vitro Evaluation," *Biomaterials*, 2001, pp. 151-163, vol. 22, Elsevier Science Ltd.

Wissink, M.J., et al., "Improved Endothelialization of Vascular Grafts by Local Release of Growth Factor from Heparinized Collagen Matrices," *J. Control Release*, 2000, pp. 103-114, vol. 64.

Xu, G., et al., "Free Electron Laser Induces Specific Immobilization of Heparin on Polysulfone Films," *Biomater. Sci. Polym. Ed.*, 2001, pp. 503-514, vol. 12(5).

Yannas, I.V. and Tobolsky, A.V., "Cross-Linking of Gelatine by Dehydration," *Nature*, 1967, pp. 509-510, vol. 215(100).

Yaylaoğlu, M.B., et al., "Development of a Calcium Phosphate-Gelatin Composite as a Bone Substitute and its Use in Drug Release," *Biomaterials*, 1999, pp. 711-719, vol. 20.

Zaleskas, J.M., "Growth Factor Regulation of Smooth Muscle Actin Expression and Contraction of Human Articular Chondrocytes and Meniscal Cells in a Collagen-GAG Matrix," *Exp. Cell Res.*, 2001, pp. 21-31, vol. 270.

Zhao, H. and Heindel, N., "Determination of Degree of Substitution of Formyl Groups in Polyaldehyde by the Hydroxylamine Hydrochloride Method," *Pharmaceutical Research*, 1991, pp. 400-402, vol. 8(3), Plenum Publishing Corporation.

Zhang et al., "Inverted-Colloidal-Crystal Hydrogel Matrices as Three-Dimensional Cell Scaffolds," *Adv. Funct. Mater.* 2005, pp. 725-731, vol. 15, No. 5.

Zimmermann, J., et al., "Novel Hydrogels as Supports for in vitro Cell Growth: poly(ethylene glycol)- and Gelatine-Based (meth)acrylamidopeptide Macromonomers," *Biomaterials*, 2002, pp. 2127-2134, vol. 23, Elsevier Science Ltd.

\* cited by examiner

BONE IMPLANT MATERIALS COMPRISING CROSS-LINKED BIOACTIVE HYDROGEL MATRICES

CROSS-REFERENCE TO RELATED APPLICATIONS

This application is a division of U.S. patent application Ser. No. 13/793,644, filed Mar. 11, 2013, now U.S. Pat. No. 8,957,050, which is a continuation of U.S. patent application Ser. No. 13/252,500, filed Oct. 4, 2011, now U.S. Pat. No. 8,664,202, which is a division of U.S. patent application Ser. No. 12/782,322, filed May 18, 2010, now U.S. Pat. No. 8,053,423, which is a division of U.S. patent application Ser. No. 10/372,643, filed Feb. 21, 2003, now U.S. Pat. No. 7,799,767, which claims priority to Provisional Application Ser. No. 60/358,625, filed Feb. 21, 2002. All of the foregoing applications are incorporated herein by reference in their entirety.

FIELD OF THE INVENTION

The present invention relates to cross-linked bioactive hydrogel matrices that are appropriate for use in therapeutic methods based on the induction of localized vasculogenesis, wound healing, tissue repair, and tissue regeneration.

BACKGROUND OF THE INVENTION

The replacement or repair of damaged or diseased tissues or organs by implantation has been, and continues to be, a long-standing goal of medicine towards which tremendous progress has been made. Working toward that goal, there is an increasing interest in tissue engineering techniques where biocompatible, biodegradable materials are used as a support matrix, as a substrate for the delivery of cultured cells, or for three-dimensional tissue reconstruction (Park, S., "Characterization of porous collagen/hyaluronic acid scaffold modified by 1-ethyl-3-(3-dimethylaminopropyl) carbodiimide cross-linking" *Biomaterials* 23:1205-1212 (2002)). However, one of the most serious problems restricting the use of implanted materials is the wound healing response by the body elicited by the implanted foreign materials (Ratner, B. D., "Reducing capsular thickness and enhancing angiogenesis around implant drug release systems" *Journal of Controlled Release* 78:211-218 (2002)).

Biocompatibility is defined as the appropriate response of the host to a foreign material used for its intended application. Biocompatibility further refers to the interaction between the foreign material and the tissues and physiological systems of the patient treated with the foreign material. Protein binding and subsequent denaturation as well as cell adhesion and activation have been invoked as determinants of a material's biocompatibility. Biocompatibility also implies that the implant avoids detrimental effects from the host's various protective systems and remains functional for a significant period of time. In vitro tests designed to assess cytotoxicity or protein binding are routinely used for the measurement of a material's potential biocompatibility. In other words, the biocompatibility of a material is dependent upon its ability to be fully integrated with the surrounding tissue following implantation.

Previous research has shown that the specific interactions between cells and their surrounding extracellular matrix play an important role in the promotion and regulation of cellular repair and replacement processes (Hynes, S. O., "Integrins: a family of cell surface receptors" *Cell* 48:549-554 (1987)). Consequently, there has been a heightened interest in work related to biocompatible polymers useful in therapeutic applications. One particular class of polymers that have proven useful for such applications, including contact lens materials, artificial tendons, matrices for tissue engineering, and drug delivery systems, is hydrogels (Schacht, E., "Hydrogels prepared by crosslinking of gelatin with dextran dialdehyde" *Reactive & Functional Polymers* 33:109-116 (1997)). Hydrogels are commonly accepted to be materials consisting of a permanent, three-dimensional network of hydrophilic polymers with water filling the space between the polymer chains. Hydrogels may be obtained by copolymerizing suitable hydrophilic monomers, by chain extension, and by cross-linking hydrophilic pre-polymers or polymers.

Prior work has shown that a thermoreversible hydrogel matrix, which is liquid near physiologic temperatures, elicits vasculogenesis and modulates wound healing in dermal ulcers (Usala A. L. et al. "Induction of fetal-like wound repair mechanisms in vivo with a novel matrix scaffolding" *Diabetes* 50 (Supplement 2): A488 (2001), and Usala A. L. et al., "Rapid Induction of vasculogenesis and wound healing using a novel injectable connective tissue matrix" *Diabetes* 49 (Supplement 1): A395 (2000)). This bioactive hydrogel material has also been shown to improve the healing in response to implanted foreign materials; demonstrating a decrease in the surrounding fibrous capsule thickness and a persistent increase in blood supply immediately adjacent to implanted materials exposed to this thermoreversible hydrogel. (Ravin A. G. et al., "Long- and Short-Term Effects of Biological Hydrogels on Capsule Microvascular Density Around Implants in Rats" *J Biomed Mater Res* 58(3):313-8 (2001)). However the use of such a bioactive thermoreversible hydrogel in therapeutic applications requiring three-dimensional and thermal stability is not practical because the hydrogel is molten at physiologic temperatures. Accordingly, there is a need for a bioactive material that is stable at body temperatures and thus appropriate for use either as a medical device or in medical applications, particularly those intended for use in mammals.

A particular biopolymer for use in medical applications is disclosed in U.S. Pat. No. 6,132,759, which relates to a medicament containing a biopolymer matrix comprising gelatin cross-linked with oxidized polysaccharides. The biopolymer of the '759 patent is claimed to be useful for treating skin wounds or dermatological disorders when a wound healing stimulating drug is incorporated therein. Similarly, U.S. Pat. No. 5,972,385 describes a matrix formed by reacting a modified polysaccharide with collagen that may subsequently be used for tissue repair when combined with growth factors. Various additional publications have described polymers and co-polymers for use in medical applications, such as drug delivery, tissue regeneration, wound healing, wound dressings, adhesion barriers, and wound adhesives. (See, for example, Draye, J. P. et al., "In vitro release characteristics of bioactive molecules from dextran dialdehyde cross-linked gelatin hydrogel films" *Biomaterials* 19:99-107 (1998); Draye, J. P. et al., "In vitro and in vivo biocompatibility of dextran dialdehyde cross-linked gelatin hydrogel films" *Biomaterials* 19:1677-1687 (1998); Kawai, K. et al., "Accelerated tissue regeneration through incorporation of basic fibroblast growth factor impregnated gelatin microspheres into artificial dermis"*Biomaterials* 21:489-499 (2000); Edwards, G. A. et al., "In vivo evaluation of collagenous membranes as an absorbable adhesion barrier" *Biomed. Mater. Res.* 34:291-297 (1997); U.S. Pat.

No. 4,618,490; and U.S. Pat. No. 6,165,488.) Such biocompatible polymers, however, are generally only therapeutically effective when combined with other therapeutic agents, such as growth factors, clotting factors, antibiotics, and other drugs.

Several biocompatible polymers previously known are based at least in part on collagen or collagen derived material. Additionally, other known biocompatible polymers are based on polysaccharides, particularly dextran. In some instances, biopolymers have been formed by cross-linking gelatin and dextran; however, the usefulness of such polymers for long-temi use in the body has not been shown. It is well documented that gelatin and dextran are incompatible in aqueous solution making it difficult to produce co-polymers that are stable at body temperatures.

Thus, there still remains a need for stabilized, bioactive hydrogels that are useful for medical applications where stable, long-term use in the body is desired.

BRIEF SUMMARY OF THE INVENTION

A stabilized cross-linked bioactive hydrogel matrix useful as a therapeutic gel or paste is provided. The viscosity of the bioactive hydrogel of the invention may be varied over a wide range by controlling the process conditions using parameters well known to those skilled in the art. These bioactive hydrogels may be used either as therapeutic medical devices or as adjuvants to other forms of therapy requiring a modulation of localized wound healing and tissue integration. The hydrogel matrices of the invention comprise a first high molecular weight component and a second high molecular weight component covalently cross-linked to the first high molecular weight component, wherein the first high molecular weight component and the second high molecular weight component are each selected from the group consisting of polyglycans cans and polypeptides. The matrix further comprises one or more enhancing agents, such as polar amino acids, amino acid analogues, amino acid derivatives, intact collagen, and divalent cation chelators, such as ethylenediaminetetraacetic acid (EDTA) or salts thereof. In a preferred embodiment, the composition comprises a high molecular weight polyglycan covalently bonded to a high molecular weight polypeptide. The two high molecular weight components are preferably dextran and gelatin. Preferred enhancing agents include polar amino acids, such as cysteine, arginine, lysine, and glutamic acid, EDTA or salts thereof, and mixtures or combinations thereof.

A method for preparing a stabilized cross-linked bioactive hydrogel matrix is also provided. The method comprises providing a mixture of a first high molecular weight component, a second high molecular weight component, and an enhancing agent, and reacting the first high molecular weight component with the second high molecular weight component under conditions sufficient to covalently cross-link the first high molecular weight component to the second high molecular weight component. As would be understood, the two high molecular weight components can be cross-linked during or after addition of the enhancing agent(s).

In another aspect, the present invention provides a method for using a stabilized cross-linked bioactive hydrogel matrix for enhancing tissue regeneration. The method comprises the steps of identifying a specific site in need of tissue regeneration and administering a therapeutically effective amount of a stabilized cross-linked bioactive hydrogel matrix, as described above, to the identified site.

In yet another aspect, a method for using a stabilized cross-linked bioactive hydrogel matrix for adding bulk to tissue is provided. The method comprises the steps of identifying a specific site in need of added tissue bulk and administering a therapeutically effective amount of a stabilized cross-linked bioactive hydrogel matrix, as described above, to the identified site.

In still another aspect, the invention provides a method for preparing a bone implant using a stabilized cross-linked bioactive hydrogel matrix of the present invention. The method comprises the steps of providing an amount of an osteoconductive or osteoinductive material, such as calcium aluminate, hydroxyapatite, alumina, zirconia, aluminum silicates, calcium phosphate, bioactive glass, ceramics, collagen, autologous bone, allogenic bone, xenogenic bone, coralline, or derivates or combinations thereof, providing a stabilized cross-linked bioactive hydrogel matrix as described above, combining the osteoconductive or osteoinductive material with the hydrogel matrix to form a pourable and castable composite paste, casting the paste into a shaped mold, allowing the paste in the shaped mold to harden, and removing the cast paste from the shaped mold.

In a further aspect of the present invention is provided a method for using a stabilized cross-linked bioactive hydrogel matrix in combination with viable tissue cells for therapeutic treatment.

In another aspect of the present invention is provided a method for using a stabilized cross-linked bioactive hydrogel matrix for treating a wound, for example, as a wound covering or as a tissue sealant.

BRIEF DESCRIPTION OF THE DRAWINGS

Figure 1:
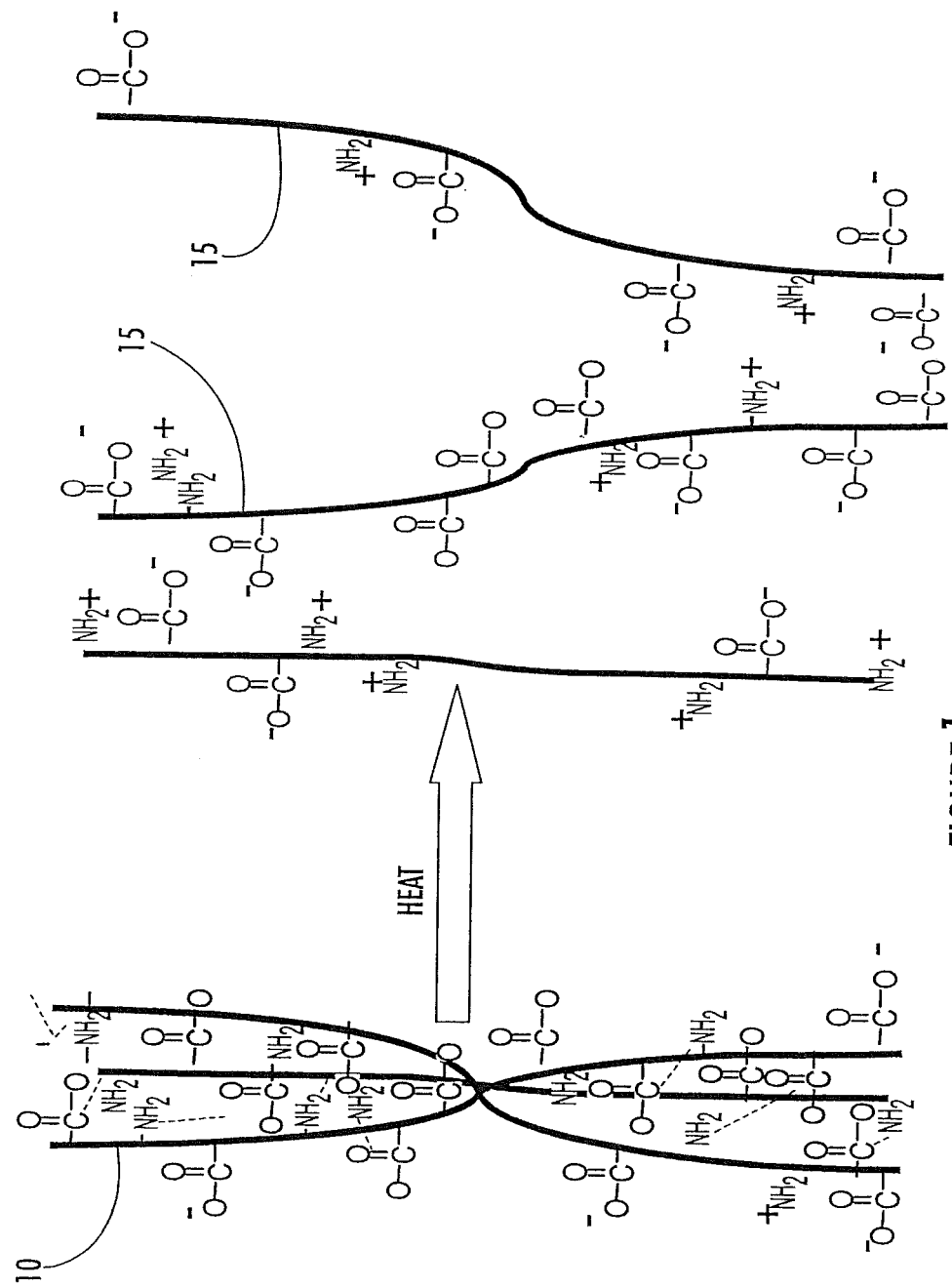
Figure 2:
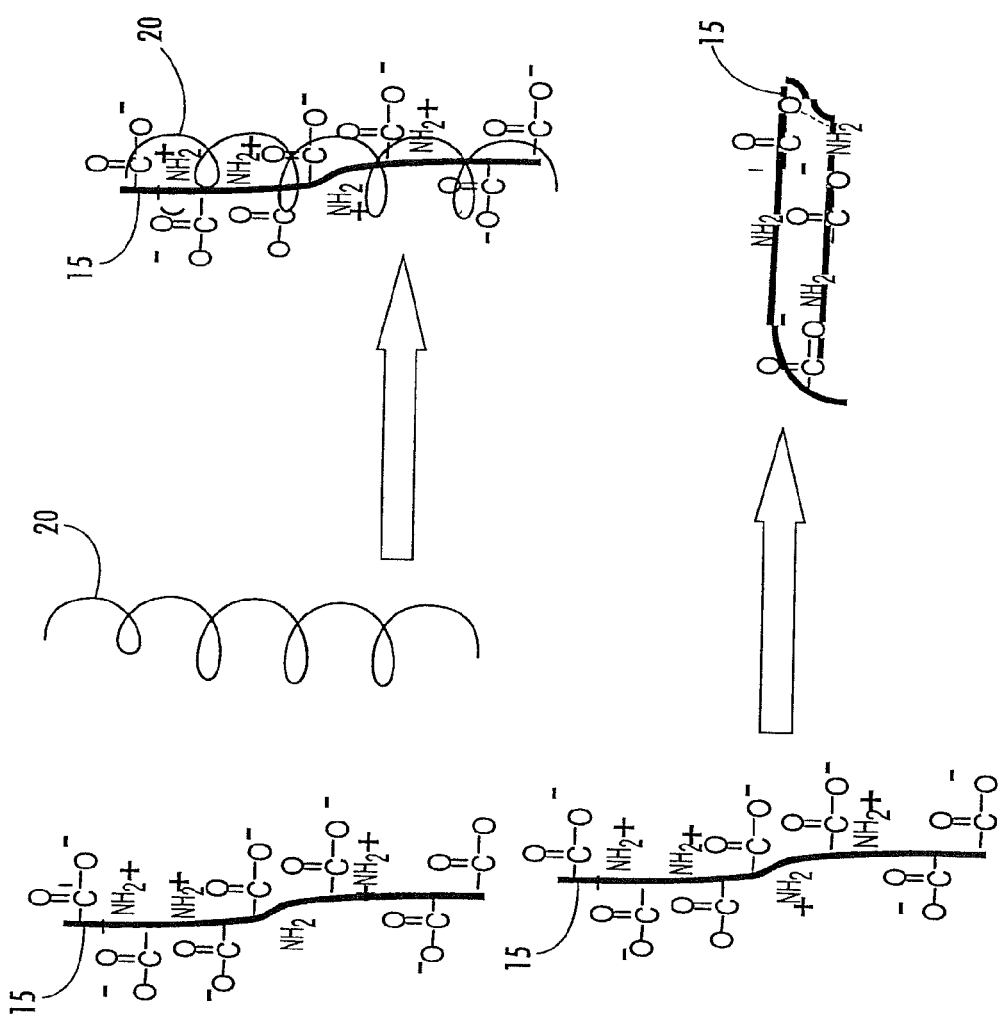
Figure 3:
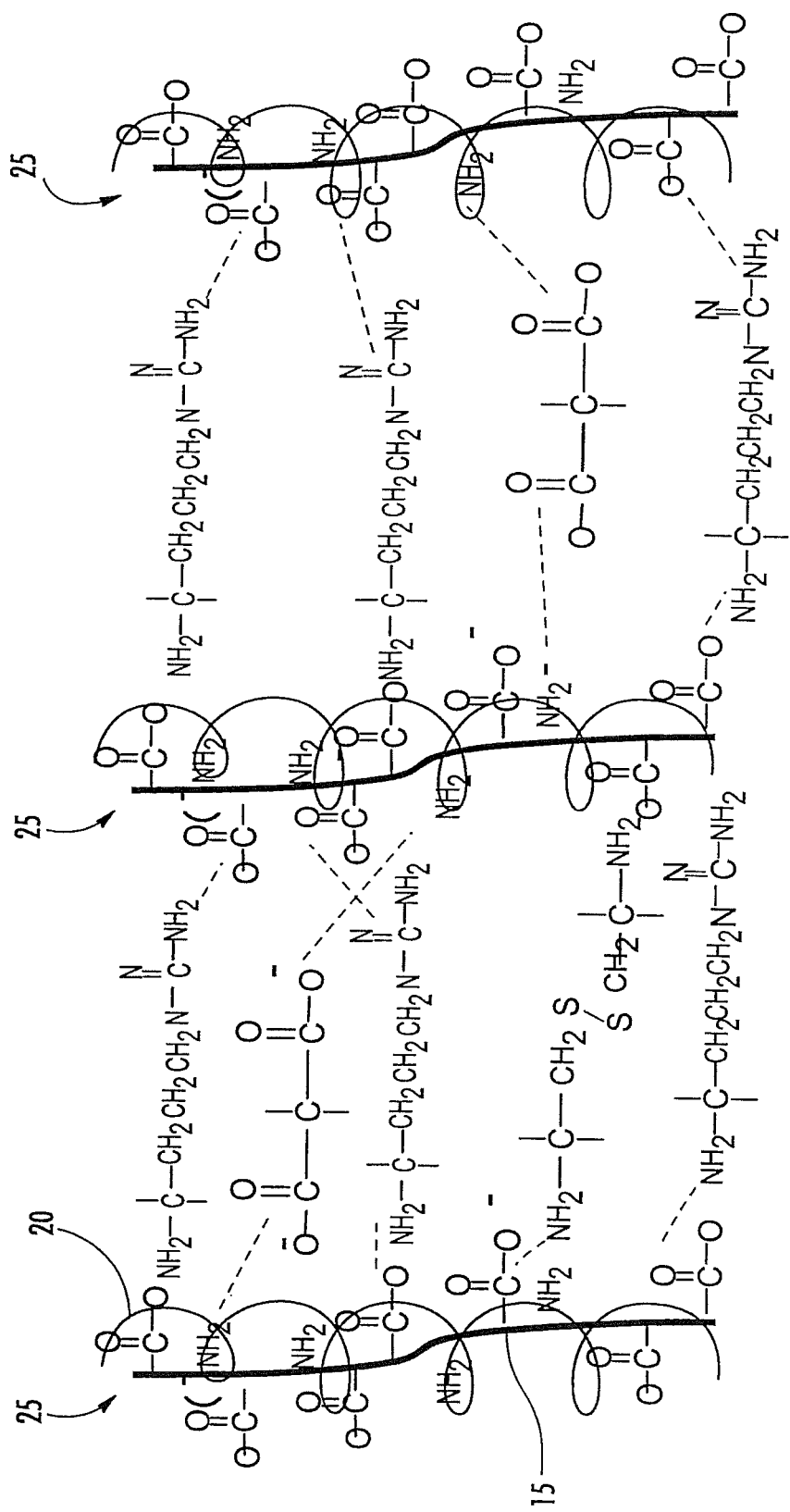
Figure 4:
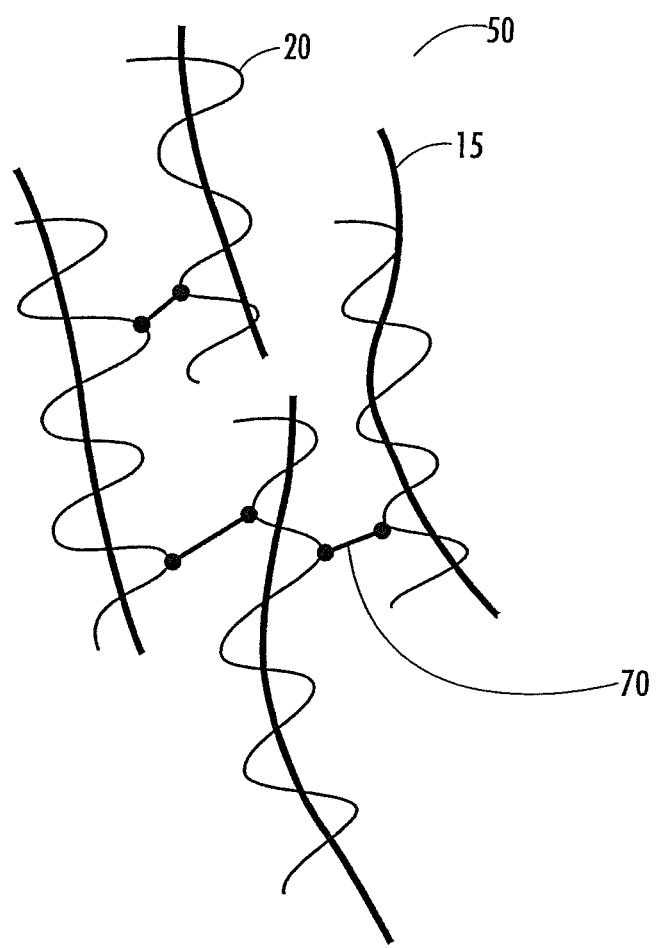
Figure 5:
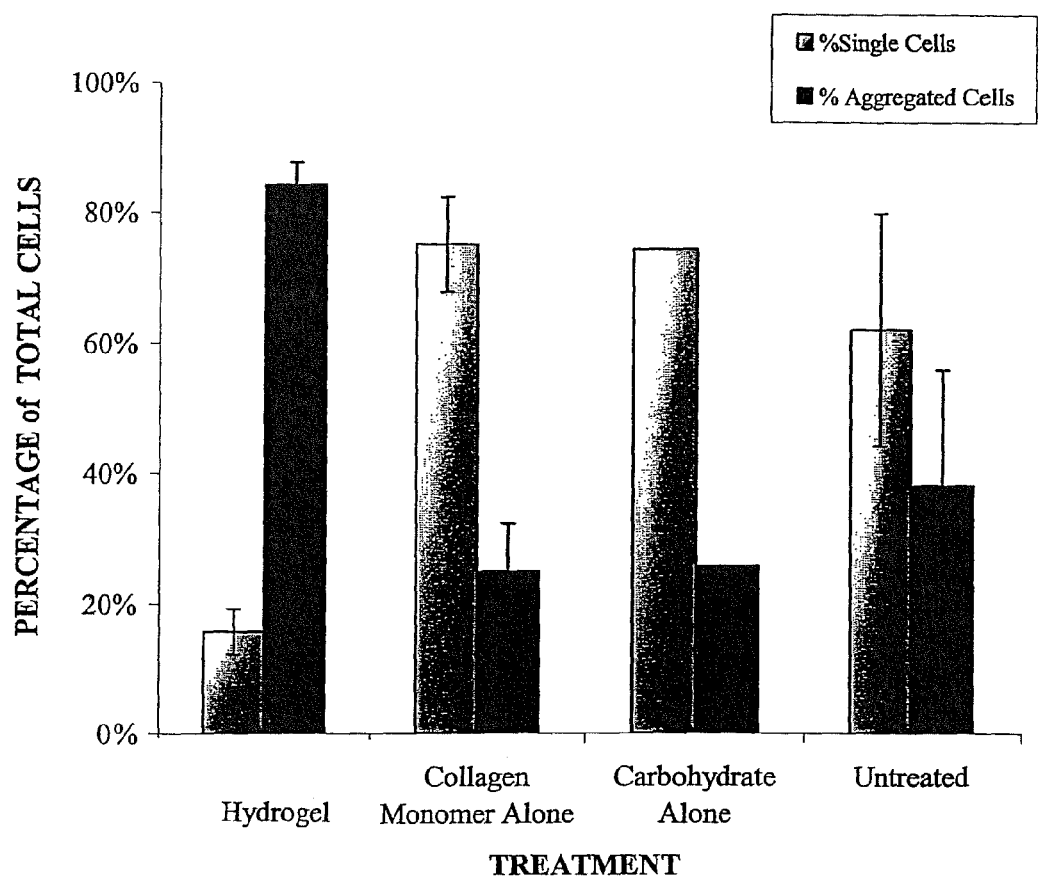
Figure 6:
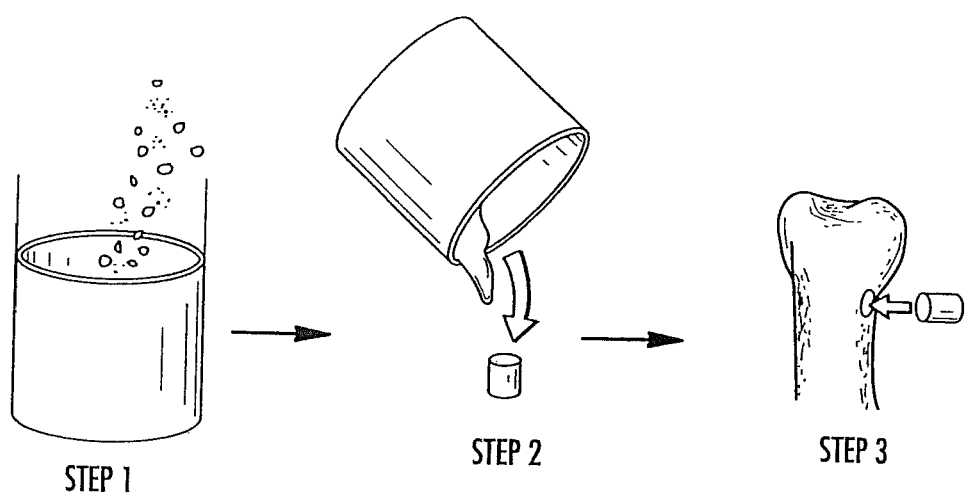
Figure 7:
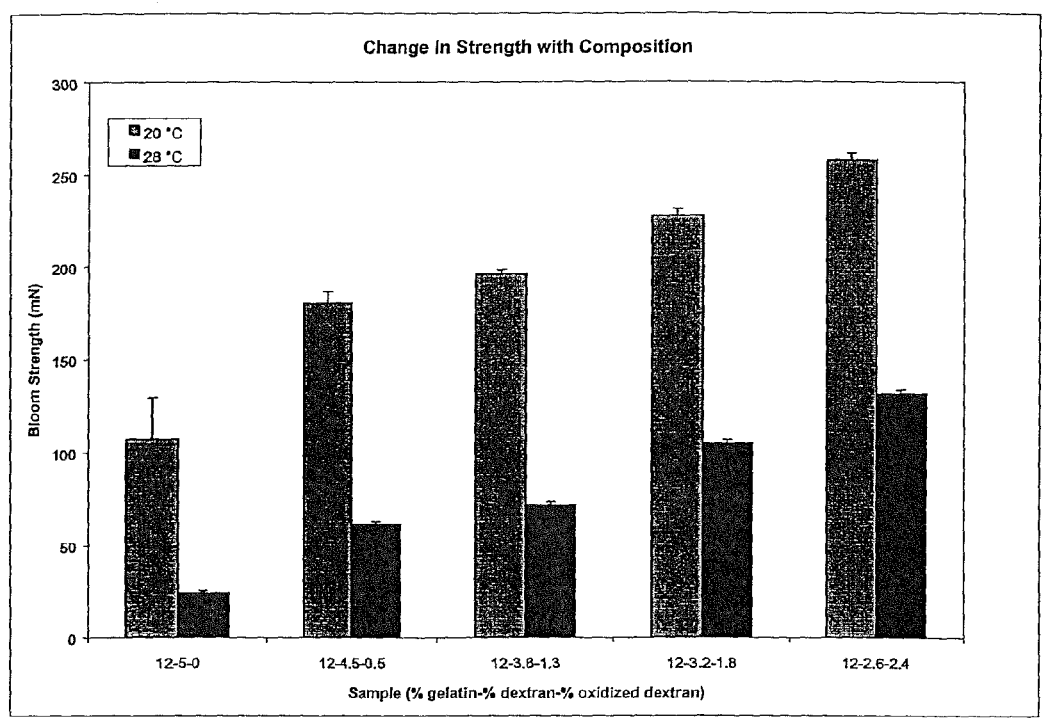

Having thus described the invention in general terms, reference will now be made to the accompanying drawings, which are not necessarily drawn to scale, and wherein:

FIG. 1 illustrates formation of open alpha chains derived from collagen monomers;

FIG. 2A illustrates the effect of the association of the alpha chains with dextran;

FIG. 2B illustrates the behavior of the alpha chains without association of the dextran;

FIG. 3 illustrates the effect of other hydrogel matrix additives;

FIG. 4 illustrates an embodiment of a covalently cross-linked gelatin/dextran matrix of the invention;

FIG. 5 illustrates graphically the effect of a hydrogel matrix in promoting cell aggregation;

FIG. 6 illustrates the use of a cross-linked embodiment of the bioactive matrix of the present invention in bone repair; and FIG. 7 illustrates graphically the relationship of the overall strength of the cross-linked hydrogel matrix to the amount of dextran oxidation.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The formulation of a thermoreversible hydrogel matrix providing a cell culture medium and composition for preserving cell viability is taught by U.S. Pat. No. 6,231,881, herein incorporated by reference in its entirety. Additionally, a hydrogel matrix useful in promoting vascularization is provided in U.S. Pat. No. 6,261,587, herein incorporated by reference in its entirety. The thermoreversible hydrogel matrix taught by these references is a gel at storage temperatures and molten at physiologic temperatures, and comprises a combination of a collagen-derived component, such as gelatin, a long chain polyglycan, such as dextran, and effective amounts of other components, such as polar amino acids. The thermoreversible hydrogel matrix taught by these references is discussed below in connection with FIGS. 1-3.

Collagen is a major protein component of the extracellular matrix of animals. Collagen is assembled into a complex fibrillar organization. The fibrils are assembled into bundles that form the fibers. The fibrils are made of five microfibrils placed in a staggered arrangement. Each microfibril is a collection of collagen rods. Each collagen rod is a right-handed triple-helix, each strand being itself a left-handed helix. Collagen fibrils are strengthened by covalent intra- and intermolecular cross-links which make the tissues of mature animals insoluble in cold water. When suitable treatments are used, collagen rods are extracted and solubilized where they keep their conformation as triple-helices. This is denatured collagen and differs from the native form of collagen, but has not undergone sufficient thermal or chemical treatment to break the intramolecular stabilizing covalent bonds found in collagen. When collagen solutions are extensively heated, or when the native collagen containing tissues are subjected to chemical and thermal treatments, the hydrogen and covalent bonds that stabilize the collagen helices are broken, and the molecules adopt a disordered conformation. By breaking these hydrogen bonds, the polar amine and carboxylic acid groups are now available for binding to polar groups from other sources or themselves. This material is gelatin and is water-soluble at 40-45° C.

As noted above, gelatin is a form of denatured collagen, and is obtained by the partial hydrolysis of collagen derived from the skin, white connective tissue, or bones of animals. Gelatin may be derived from an acid-treated precursor or an alkali-treated precursor. Gelatin derived from an acid-treated precursor is known as Type A, and gelatin derived from an alkali-treated precursor is known as Type B. The macromolecular structural changes associated with collagen degradation are basically the same for chemical and partial thermal hydrolysis. In the case of thermal and acid-catalyzed degradation, hydrolytic cleavage predominates within individual collagen chains. In alkaline hydrolysis, cleavage of inter- and intramolecular cross-links predominates.

FIG. 1 illustrates the hydrolytic cleavage of the tropocollagen 10, forming individual polar alpha chains of gelatin 15. Heating tropocollagen 10 disrupts the hydrogen bonds that tightly contain the triple stranded monomers in mature collagen.

FIGS. 2A-2B illustrate stabilization of the matrix monomeric scaffolding by the introduction of a long-chain polyglycan, such as dextran 20. As depicted in FIG. 2A, the dextran 20 serves to hold open the gelatin 15, that has been previously heated, by interfering with the natural predisposition of the gelatin 15 to fold upon itself and form hydrogen bonds between its polar groups. In the absence of dextran 20, as shown in FIG. 2B, when the gelatin 15 begins to cool, it will form hydrogen bonds between the amino and carboxylic acid groups within the linear portion of the monomer and fold upon itself, thus limiting available sites for cellular attachment.

The thermoreversible matrix contains a polyglycan, such as dextran, at a therapeutically effective concentration ranging from, for example, about 0.01 to about 10 mM, preferably about 0.01 to about 1 mM, most preferably about 0.01 to about 0.1 mM. In one embodiment, dextran is present at a concentration of about 0.09 mM.

The thermoreversible matrix also contains gelatin, at a therapeutically effective concentration ranging from, for example, about 0.01 to about 40 mM, preferably about 0.05 to about 30 mM, most preferably about 1 to 5 mM. Advantageously, the gelatin concentration is approximately 1.6 mM.

In order to increase cell binding, intact collagen may be added in small amounts to the thermoreversible matrix in order to provide additional structure for the cells contained in the matrix. The final concentration of intact collagen is from about 0 to about 5 mM, preferably about 0 to about 2 mM, most preferably about 0.05 to about 0.5 mM. In one embodiment, the concentration of intact collagen is about 0.11 mM.

The thermoreversible matrix may additionally contain an effective amount of polar amino acids, which are commonly defined to include tyrosine, cysteine, serine, threonine, asparagine, glutamine, asparatic acid, glutamic acid, arginine, lysine, and histidine. For application in the present invention, the amino acids are preferably selected from the group consisting of cysteine, arginine, lysine, histidine, glutamic acid, aspartic acid and mixtures thereof, or derivatives or analogues thereof. By amino acid is intended all naturally occurring alpha amino acids in both their D and L stereoisomeric forms, and their analogues and derivatives. An analog is defined as a substitution of an atom or functional group in the amino acid with a different atom or functional group that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine. The total concentration of all polar amino acids is generally between about 3 to about 150 mM, preferably about 10 to about 65 mM, and more preferably about 15 to about 40 mM.

Advantageously, the added polar amino acids comprise L-cysteine, L-glutamic acid, L-lysine, and L-arginine. The final concentration of L-glutamic acid is generally about 2 to about 60 mM, preferably about 5 to about 40 mM, most preferably about 10 to about 20 mM. In one embodiment, the concentration of L-glutamic acid is about 15 mM. The final concentration of L-lysine is generally about 0.5 to about 30 mM, preferably about 1 to about 15 mM, most preferably about 1 to about 10 mM. In one embodiment, the concentration of L-lysine is about 5.0 mM. The final concentration of L-arginine is generally about 1 to about 40 mM, preferably about 1 to about 30 mM, most preferably about 5 to about 15 mM. In one embodiment, the final concentration of arginine is about 10 mM. The final concentration of L-cysteine, which provides disulfide linkages, is generally about 5 to about 500 µM, preferably about 10 to about 100 µM, most preferably about 15 to about 25 µM. In one embodiment, the final concentration of cysteine is about 20 µM.

The thermoreversible matrix is preferably based upon a physiologically compatible buffer, one embodiment being Medium 199, a common nutrient solution used for in vitro culture of various mammalian cell types (available commercially from Sigma Chemical Company, St. Louis, Mo.), which is further supplemented with additives and additional amounts of some medium components, such as supplemental amounts of polar amino acids as described above.

Advantageously, aminoguanidine may be added to this formulation; however, other L-arginine analogues may also be used in the present invention, such as N-monomethyl L-arginine, N-nitro-L-arginine, or D-arginine. The final concentration of aminoguanidine is generally about 5 to about 500 µM, preferably about 10 to about 100 µM, most preferably about 15 to about 25 µM. In one embodiment, the final concentration is about 20 µM.

Additionally, the matrix may include one or more divalent cation chelators, which increase the rigidity of the matrix by forming coordinated complexes with any divalent metal ions present. The formation of such complexes leads to the increased rigidity of the matrix by removing the inhibition of hydrogen bonding between —$NH_2$ and —COOH caused by the presence of the divalent metal ions. A preferred example of a divalent cation chelator that is useful in the present invention is ethylenediaminetetraacetic acid (EDTA) or a salt thereof. The concentration range for the divalent cation chelator, such as EDTA, is generally about 0.01 to about 10 mM, preferably 1 to about 8 mM, most preferably about 2 to about 6 mM. In a one embodiment, EDTA is present at a concentration of about 4 mM.

FIG. 3 illustrates the effect of polar amino acids and L-cysteine added to stabilize the units 25, formed by the gelatin 15 and dextran 20, by linking the exposed monomer polar sites to, for example, arginine's amine groups or glutamic acid's carboxylic acid groups. Furthermore, disulfide linkages can be formed between L-cysteine molecules (thereby forming cystine), which in turn form hydrogen bonds to the gelatin 15.

The mechanical and thermal characteristics of the thermoreversible hydrogel described above are to a large extent determined by the thermomechanical properties of one of its major components, gelatin. Gelatin-based matrices typically are molten at near physiologic temperatures and hence cannot be expected to have the requisite durability and mechanical properties when required for implantation as a medical device in certain applications. Therefore, it is imperative to stabilize these gels through a variety of intermolecular interactions including hydrogen bonding, electrostatic or polar amino acid mediated bonding, hydrophobic bonding and covalent bonding. Although not wishing to be bound by theory, it is believed that the types of bonding mechanisms described above in association with a long chain polyglycan stabilize polypeptides such as gelatin. For example, as discussed in more detail below, the positively charged polar groups of the collagen-derived alpha chains are then able to associate with the negatively charged hydroxyl groups of the repeating glucose units found in, for example, dextran. The gelatin and dextran form a composite bioactive hydrogel containing macromolecular proteoglycan-type structures.

Unlike the prior art thermoreversible matrix discussed above, the present invention provides stabilized compositions comprising a cross-linked bioactive hydrogel matrix that can be used, for example, to promote wound healing or vasculogenesis. The present invention is also directed to a method for preparing a cross-linked bioactive hydrogel matrix that is therapeutically useful at physiological temperatures. By "bioactive" is intended the ability to facilitate or discourage a cellular or tissue response of a host to foreign materials introduced to the body. Examples include, but are not limited to, induction of vasculogenesis, inhibition of the formation of a foreign body response, promotion of cellular attachment to the scaffold material, and promotion of tissue regeneration. The term "stabilized" or "stable" is intended to refer to compositions that are water-swellable, poorly soluble, solid or semi-solid materials at physiological temperature (i.e., about 37° C.) and in physiological fluids (e.g., aqueous body fluids having a physiological pH of about 7.4), which remain present in the host for sufficient time to achieve the intended response.

The stabilized bioactive hydrogel matrix of the invention is formed from at least two high molecular weight components. The high molecular weight components of the bioactive hydrogel matrix are selected from the group consisting of high molecular weight polyglycans, high molecular weight polypeptides, and combinations thereof. By high molecular weight polyglycan is intended any polysaccharide consisting of more than about 10 monosaccharide residues joined to each other by glycosidic linkages. The polyglycan may consist of the same monosaccharide residues, or various monosaccharide residues or derivatives of monosaccharide residues. Dextran, a preferred polysaccharide, solely comprises glucose residues. Dextran typically comprises linear chains of $\alpha(1 \rightarrow 6)$-linked D-glucose residues, often with $\alpha(1 \rightarrow 2)$- or $\alpha(1 \rightarrow 3)$-branches. Native dextran, produced by a number of species of bacteria of the family Lactobacilliaceae, is a polydisperse mixture of components.

The polyglycan component preferably has a molecular weight range of about 2,000 to about 8,000,000 Da, more preferably about 20,000 to about 1,000,000 Da. Unless otherwise noted, molecular weight is expressed herein as number average molecular weight ($M_n$), which is defined as $$\frac{\sum NiMi}{\sum Ni},$$

wherein Ni is the number of polymer molecules (or the number of moles of those molecules) having molecular weight Mi.

Any polysaccharide, including glycosaminoglycans (GAGs) or glucosaminoglycans, with suitable viscosity, molecular mass and other desirable properties may be utilized in the present invention. By glycosaminoglycan is intended any glycan (i.e., polysaccharide) comprising an unbranched polysaccharide chain with a repeating disaccharide unit, one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. By glycosaminoglycan is intended any glycan (i.e. polysaccharide) containing predominantly monosaccharide derivatives in which an alcoholic hydroxyl group has been replaced by an amino group or other functional group such as sulfate or phosphate. An example of a glycosaminoglycan is poly-N-acetyl glycosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate.

By high molecular weight polypeptide is intended any tissue-derived or synthetically produced polypeptide, such as collagens or collagen-derived gelatins. Although collagen-derived gelatin is the preferred high molecular weight polypeptide component, other gelatin-like components characterized by a backbone comprised of sequences of amino acids having polar groups that are capable of interacting with other molecules can be used. For example, keratin, decorin, aggrecan, glycoproteins (including proteoglycans), and the like could be used to produce the polypeptide component. In one embodiment, the polypeptide component is porcine gelatin from partially hydrolyzed collagen derived from skin tissue. Polypeptides derived from other types of tissue could also be used. Examples include, but are not limited to, tissue extracts from arteries, vocal chords, pleura, trachea, bronchi, pulmonary alveolar septa, ligaments, auricular cartilage or abdominal fascia; the reticular network of the liver; the basement membrane of the kidney; or the neurilemma, arachnoid, dura mater or pia mater of the nervous system. Purified polypeptides including, but not limited to, laminin, nidogen, fibulin, and fibrillin or protein mixtures such as those described by U.S. Pat. No. 6,264,992 and U.S. Pat. No. 4,829,000, extracts from cell culture broth as described by U.S. Pat. No. 6,284,284, submucosal tissues such as those described in U.S. Pat. No. 6,264,992, or gene products such as described by U.S. Pat. No. 6,303,765 may also be used. Another example of a suitable high molecular weight polypeptide is a fusion protein formed by genetically engineering a known reactive species onto a protein. The polypeptide component preferably has a molecular weight range of about 3,000 to about 3,000,000 Da, more preferably about 30,000 to about 300,000 Da.

In a preferred embodiment, gelatin and dextran are components of the bioactive matrix of the present invention. For ease of describing the invention, the terms "gelatin" and "dextran" are used throughout with the understanding that various alternatives as described above, such as other polyglycan and polypeptide components readily envisioned by those skilled in the art, are contemplated by the present invention.

In one embodiment of the present invention, as illustrated in FIG. 4, dextran 20 is covalently crosslinked to gelatin 15 by linkages 70, thereby forming a crosslinked network 50. The linkages 70 either result from reaction of functional groups on the gelatin 15 with functional groups on the dextran 20, or result from reaction of a bifunctional cross-linker molecule with both the dextran 20 and gelatin 15. As explained in greater detail below, one method of crosslinking gelatin and dextran is to modify the dextran molecules 20, such as by oxidation, in order to form functional groups suitable for covalent attachment to the gelatin 15. This stabilized cross-linked bioactive network 50 yields therapeutically useful gels and pastes that are insoluble in physiologic fluids at physiological temperatures. No additional substrate or surface is required. The so-formed gels and pastes are appropriate for the development of therapeutic methods based on the induction of a localized vasculogenesis, wound healing, tissue repair, and regeneration. Such bioactive hydrogel gels and pastes may be used, for example, to repair ischemic regions of the heart or peripheral vessels, facilitate bone repair, or to provide a localized scaffolding for wound healing and tissue repair.

In one embodiment of the method of making the cross-linked hydrogel matrix, one of the high molecular weight components must be modified to form reactive groups suitable for cross-linking. For instance, the dextran or other polyglycan component can be modified, such as by oxidation, in order to cross-link with the gelatin component. One known reaction for oxidizing polysaccharides is periodate oxidation. The basic reaction process utilizing periodate chemistry is well known and appreciated by those skilled in the art. Periodate oxidation is described generally in *Affinity Chromatography: A Practical Approach*, Dean, et al., IRL Press, 1985 ISBN0-904147-71-1, which is incorporated by reference in its entirety. The oxidation of dextran by the use of periodate-based chemistry is described in U.S. Pat. No. 6,011,008, which is herein incorporated by reference in its entirety.

In periodate oxidation, polysaccharides may be activated by the oxidation of the vicinal diol groups. With polyglycans, this is generally accomplished through treatment with an aqueous solution of a salt of periodic acid, such as sodium periodate ($NaIO_4$), which oxidizes the sugar diols to generate reactive aldehyde groups (e.g. dialdehyde residues). This method is a rapid, convenient alternative to other known oxidation methods, such as those using cyanogen bromide. Polyglycans activated by periodate oxidation may be stored at 4° C. for several days without appreciable loss of activity.

Polyglycan materials, such as dextran, activated in this manner readily react with materials containing amino groups, such as gelatin, producing a cross-linked material through the formation of Schiff's base links. A Schiff base is a name commonly used to refer to the imine formed by the reaction of a primary amine with an aldehyde or ketone. The aldehyde groups formed on the cellulosic surface react with most primary amines between pH values from about 4 to about 6. The Schiff's base links form between the dialdehyde residues of the polyglycan and the free amino groups on the protein. The cross-linked product may subsequently be stabilized (i.e. formation of stable amine linkages) by reduction with a borohydride, such as sodium borohydride ($NaBH_4$) or sodium cyanoborohydride ($NaBH_3CN$). The residual aldehyde groups may be consumed with ethanolamine or other amine containing species to further modify the cross-linked matrix. Other methods known to those skilled in the art may be utilized to provide reactive groups on either one or both of the high molecular weight components of the matrix.

In the present invention, periodate chemistry is used with dextran to fool a multifunctional polymer that can then react with gelatin and enhancing agents present during the manufacturing process. The periodate reaction leads to the formation of polyaldehyde polyglycans that are reactive with primary amines. For example, high molecular weight polypeptides and high molecular weight polyglycans may form covalent hydrogel complexes that are colloidal or covalently cross-linked gels. Covalent bonding occurs between reactive groups of the dextran and reactive groups of the gelatin component. The reactive sites on the gelatin include amine groups provided by arginine, asparagine, glutamine, and lysine. These amine groups react with the aldehyde or ketone groups on the dextran to form a covalent bond. These hydrogels can be readily prepared at temperatures from about 34° C. to about 90° C. Additionally, the hydrogels can be prepared at a pH range of from about 5 to about 9, preferably from about 6 to about 8, and most preferably from about 7 to about 7.6.

By controlling the extent of dextran activation and the reaction time, one can produce stabilized biomimetic scaffolding materials of varying viscosity and stiffness. By "biomimetic" is intended compositions or methods imitating or stimulating a biological process or product. Some biomimetic processes have been in use for several years, such as the artificial synthesis of vitamins and antibiotics. More recently, additional biomimetic applications have been proposed, including nanorobot antibodies that seek and destroy disease-causing bacteria, artificial organs, artificial arms, legs, hands, and feet, and various electronic devices. The biomimetic scaffolding materials of the present invention yield therapeutically useful gels and pastes that are stable at about 37° C., or body temperature. These gels are capable of expansion and/or contraction, but will not dissolve in aqueous solution.

As an alternate method for forming the crosslinked dextran/gelatin network, a multifunctional cross-linking agent may be utilized as a reactive moiety that covalently links the gelatin and dextran chains. Such bifunctional cross-linking agents may include glutaraldehyde, epoxides (e.g., bis-oxiranes), oxidized dextran, p-azidobenzoyl hydrazide, N-[□-maleimidoacetoxy]succinimide ester, p-azidophenyl glyoxal monohydrate, bis-[□□(4-azidosalicylamido)ethyl] disulfide, bis[sulfosuccinimidyl]suberate, dithiobis[succinimidyl proprionate, disuccinimidyl suberate, 1-ethyl-3-[3-dimethylaminopropyl]carbodiimide hydrochloride, and other bifunctional cross-linking reagents known to those skilled in the art.

In another embodiment utilizing a cross-linking agent, polyacrylated materials, such as ethoxylated (20) trimethylpropane triacrylate, may be used as a non-specific photo-activated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine Continuous exposure of this reactive mixture to long-wavelength light (>498 nm) would produce a cross-linked hydrogel network The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydro gel matrix, include many of the additives described earlier in connection with the thermoreversible matrix discussed above. The enhancing agent can include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids is intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents can be added to the matrix composition before or during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

For example, aggregation of human fibroblasts exposed to bioactive hydrogels has been observed, while aggregation is not observed when fibroblasts are exposed to the individual components of the bioactive hydrogel. Results from numerous (over fifty) controlled experiments have shown that normal neonatal human skin fibroblasts form multi-cell aggregates when exposed to the complete thermoreversible hydrogel formulation at 37° C., while no such cell aggregating activity is demonstrated using omission formulations in which the bioactive copolymer is not formed. The aggregated cells form tightly apposed cell clusters with interdigitating cytoplasmic processes, while cells treated with formulations lacking the copolymer remain round and without surface projections. As shown in FIG. 5, in a sample of human fibroblasts exposed to a bioactive hydrogel comprising dextran and gelatin, at least 80% of the cells present were in an aggregated state while less than 20% of the cells present remained as single cells. The opposite effect was observed in samples where the human fibroblasts were exposed to collagen monomer alone, carbohydrate alone, or were left untreated. In samples exposed to collagen monomer alone, approximately 75% of the cells remained in a single cell configuration while only about 25% of the cells were in an aggregated state. Nearly the same effect was observed in samples exposed to carbohydrate alone. In samples that were left untreated, approximately 60% of the cells remained in a single cell state while only about 40% of the cells were in an aggregated state.

In each of the therapeutic uses outlined below, a therapeutically effective amount of the matrix of the invention is used. The therapeutically effective dosage amount of any specific hydrogel matrix will vary somewhat from matrix to matrix, patient to patient, use to use, and will depend upon factors such as the condition of the patient, the nature of the condition being treated, and the route of delivery. For example, a small dermal defect 1 cm in diameter and 0.5 cm deep would require approximately 0.4 cm$^3$ of stabilized cross-linked bioactive hydrogel to fill the void, stimulate vasculogenesis and tissue regeneration and have therapeutic efficacy. In contrast, a decubitus ulcer 20 cm in diameter and 5 cm deep would require approximately 1600 cm$^3$ of stabilized cross-linked bioactive hydrogel to have similar efficacy. As a general proposition the amount of cross-linked bioactive matrix required for therapeutic efficacy will be from 0.1 to 2000 cm$^3$, preferably from about 0.5 to 100 cm$^3$.

In one aspect of the invention, the stabilized cross-linked bioactive hydrogel is used for site-specific tissue regeneration, including vasculogenesis. It is known in the art to use intact collagen, gelatin, or dextran as a carrier to hold and deliver growth factors and the like in methods designed to promote tissue growth. (See, for example, Kawai, K. et al., "Accelerated tissue Regeneration Through Incorporation of Basic Fibroblast Growth Factor-Impregnated Gelatin Microspheres into Artificial Dermis" *Biomaterials* 21:489-499 (2000); and Wissink, M. J. B. et al., "Binding and Release of Basic Fibroblast Growth Factor from Heparinized Collagen Matrices" *Biomaterials* 22:2291-2299 (2001)). By contrast, the intrinsic activity of the stabilized cross-linked hydrogel of the present invention is sufficient to elicit a specific sequence of biological responses, such as promoting tissue regeneration and vasculogenesis, without the addition of exogenous drugs or growth factors. In fact, the cross-linked matrix of the invention can be substantially free, even completely free, of exogenous drugs or growth factors when used for vascularization or tissue regeneration. This intrinsically bioactive hydrogel, as a result of its unique structure, provides a cell attachment scaffold that modulates subsequent cellular activity, such as tissue regeneration and vasculogenesis.

The intrinsic bioactivity of the stabilized cross-linked hydrogel is evident in its ability to promote vasculogenesis without the use of additional growth factors, such as basic fibroblast growth factor (bFGF). The cross-linked hydrogel may be used in vivo to facilitate vascularization in damaged tissue when placed at a vascular terminus and allowed to act as a vascular scaffold upon which new vascular tissue may grow outward from the terminus. The vascular scaffold not only provides a support medium for the new vascular tissue, but it also performs the function of encouraging pro-lateral vessel growth while also providing a source of stabilization for the damaged area.

The stabilized cross-linked hydrogel behaves similarly when used in other aspects of tissue regeneration. The hydrogel provides a stabilized structural lattice that facilitates cell retention and multiplication in areas with tissue damage. This is due in part to the intrinsic bioactivity of the hydrogel, which furthers the regenerative process.

In another aspect of the invention, the stabilized cross-linked hydrogel is used as a bulking agent to provide increased dimensions to specific tissues requiring additional bulk, whether for aesthetic or functional purposes. Examples of such application include treatment of individuals with urinary incontinence and gastroesophageal reflux disease (GERD), problems commonly related to reduced sphincter tone. A sphincter is a ringlike band of muscle fibers that acts to constrict a passage or close a natural orifice. Individuals with GERD generally exhibit multiple symptoms stemming from gastric fluids that are allowed to pass from the stomach up into the esophagus because the sphincter at the base of the esophagus, which normally opens to allow materials to pass from the esophagus into the stomach and then closes, has reduced tone and fails to close completely. Individuals with GERD may be treated with medications to reduce production of gastric fluids or hasten the movement of food from the stomach into the intestines; however, severe cases often require corrective surgery, such as Nissen Fundoplication where the upper portion of the stomach is wrapped around the lower esophagus to artificially tighten the esophageal sphincter. Similarly, urinary incontinence is often a result of reduced tone in the sphincter at the base of the bladder leading into the urethra and may require multiple therapies, including surgery.

The hydrogel of the present invention may be used to treat these problems, and others related to reduced sphincter tone. The hydrogel may be injected into the sphincter either as a space-filling material or as a cell carrier to repopulate a local tissue defect thereby adding bulk, and allowing the sphincter to function normally again by using the increased bulk to make up for the reduced tone, thereby allowing the sphincter to close completely. Such treatment is made possible due to the increased stability of the cross-linked bioactive hydrogel, which maintains its structure at body temperatures and provides a biologically compatible, long-term solution that is much less invasive than alternative treatments.

In a further aspect of the present invention, the cross-linked hydrogel matrix may be combined with viable tissue cells for certain therapeutic uses. It is preferable, but not required, that the tissue cells originate from the same type of tissue for which the hydrogel matrix will be used therapeutically. The viable tissue cells can be derived from autologous tissue sources, allogenic tissue sources, or xenogenic tissue sources. The term "autologous" is meant to refer to tissue that originates from the same host. The term "allogenic" is meant to refer to tissue that originates from a source that is of the same species (i.e., human) but of non-identical genetic composition. The term "xenogenic" is meant to refer to tissue that originates from a species different from the host. Non-limiting examples of types of cells that can be used in combination with the hydrogel matrix include stem cells, bone cells, tenocytes, adipocytes, cardiomyocytes, hepatocytes, smooth muscle cells, endothelial cells, and the like. The tissue cells can be added to the hydrogel matrix prior to, during, or after cross-linking occurs.

One specific application for the hydrogel matrix combined with viable tissue cells is use of cells in the bulking agent application described above. Tissue cells that originate from the same type of tissue requiring a bulking agent can be added to the cross-linked hydrogel matrix prior to administration of the matrix to the anatomical site needing the bulking agent.

In another example, hepatocytes suspended in the matrix of the invention prior to cross-linking are injected into a patient, and cross-linked in situ. The matrix provides a) a scaffold for the immobilized cells and b) a bioactive hydrogel for rapid vascularization at the site of implant.

In yet another example, the hydrogel matrix of the invention could be used as an ex vivo culture scaffold for the development of small diameter vascular grafts, valves, or other complex tissue-engineered constructs prior to implantation in a patient. In this case, the cross-linked hydrogel serves as an organizing template directing cell growth in vitro, and can be used to develop complex organ or tissue structures through a sequence of culture steps.

In yet another aspect of the invention, the cross-linked hydrogel is mixed with other materials to form castable structures. For example, the cross-linked hydrogels can be mixed with osteoconductive or osteoinductive materials, such as calcium aluminate, hydroxyapatite, alumina, zirconia, aluminum silicates, calcium phosphate, bioactive glass, ceramics, collagen, autologous bone, allogenic bone, xenogenic bone, coralline, or derivates or combinations thereof, or other biologically produced composite materials containing calcium or hydroxyapatite structural elements. The term "osteoconductive" is meant to refer to materials that facilitate blood vessel incursion and new bone formation into a defined passive trellis structure. The term "osteoinductive" is meant to refer to materials that lead to a mitogenesis of undifferentiated perivascular mesenchymal cells leading to the formation of osteoprogenitor cells (cells with the capacity to form new bone). By "alumina" is meant the commonly held definition of materials comprised of the natural or synthetic oxide of aluminum, which may be exemplified in various forms, such as corundum. Bioactive glasses generally contain silicon dioxide ($SiO_2$) as a network former and are characterized by their ability to firmly attach to living tissue. Examples of bioactive glasses available commercially and their manufacturers include Bioglass® (American Biomaterials Corp., USA, 45% silica, 24% calcium oxide (CaO), 24.5% disodium oxide ($Na_2O$), and 6% pyrophosphate ($P_2O_5$)), Consil® (Xeipon Ltd., UK), NovaBone® (American Biomaterials Corp.), Biogran® (Orthovita, USA), PerioGlass® (Block Drug Co., USA), and Ceravital®

(E. Pfeil & H. Bromer, Germany) Corglaes® (Giltech Ltd., Ayr, UK) represents another family of bioactive glasses containing pyrophosphate rather than silicon dioxide as a network former. These glasses contain 42-49 mole % of $P_2O_5$, the remainder as 10-40 mole % as CaO and $Na_2O$.

The use of such materials as described above mixed with the stabilized cross-linked hydrogel matrix of the present invention would be expected to form castable cross-linked structures appropriate for bone repair and reconstruction as illustrated schematically in FIG. 6. As shown, the ingredients for the cross-linked bioactive hydrogel matrix of the invention are mixed in a vessel and allowed to react (i.e., cross-link) in the presence of finely divided ceramic powders, or other osteoinductive material, to form a pourable paste as shown in Step 1. The paste is cast into a shaped mold and allowed to react and harden (Step 2). The final product is removed from the mold, and in this instance, is used as a dowel for bone repair (Step 3). This device or implant is expected to induce vasculogenesis and hence better integration of the osteoinductive implant. Presumably, improving vascular supply in large bones (e.g. femur) may increase marrow production and have a therapeutic effect beyond the simple improvement in bone density and health. Solid or semi-sold gels of this type could be utilized for tissue wounds, including bone fragment wounds or non-healing fractures.

In another aspect of the invention, the stabilized cross-linked hydrogel is used as a wound healing device to protect open wounds during healing and also to promote healing by administration of the cross-linked hydrogel to the wound. The individual abilities of collagen and gelatin to play a useful role in the area of wound coverings and wound healing are well documented. Collagen is known to perform the following functions in wound healing: stop bleeding; help in wound debridement by attracting monocytes; provide a matrix for tissue and vascular growth; attract fibroblasts and help in directed migration of cells; bind with fibronectin which promotes cell binding; support cell growth, differentiation, and migration; and help in deposition of oriented and organized fibers, which increases the integrity of tissue. Similarly, gelatin also effectuates wound healing and is known to stimulate activation of macrophages and produce a high hemostatic effect. (See, for example, Hovig T. et al., "Platelet Adherence to Fibrin and Collagen" *Journal Lab and Clin. Med.* 71(1):29-39 (1968); Postlewaithe, A. E. et al., "Chemotactic Attraction of Human Fibroblasts to Type I, II, and III Collagens and collagen Derived Peptides" *Proc. Natl. Acad. Science* 177:64-65 (1978); Kleinman, H. K. et al., Role of Collagenous Matrices in the Adhesion and Growth of Cells" *The Journal of Cell Biology* 88:473-485 (1981); Dunn, G. A. and Ebendal, T., "Contact Guidance on Oriented Collagen Gels" *Exp. Cell Res.* 111:475-479 (1978); Kleinman, H. K. et al., Interactions of Fibronectin with Collagen Fibrils" *Biochemistry* 20:2325-2330 (1981); Morykwas, M. J. et al., "In Vitro and In Vivo Testing of a Collagen Sheet to Support Keratinocyte Growth for Use as a Burn Wound Covering" The Journal of Trauma 29(8):1163-1167 (1976); Emerman, J. T. and Pitelka, D. R., "Maintenance and Induction of Morphological Differentiation in Dissociated Mammary Epithelium on Floating Collagen Membranes" *In Vitro* 13(5):316-337 (1977); Doillon, C. J. et al., "Fibroblast-Collagen Sponge Interactions and Spatial Disposition of Newly Synthesized Collagen Fibers in Vitro and in Vivo" *Scanning Electron Microscopy* 3:1313-1320 (1984); and Hong, S. R. et al., "Study on Gelatin-Containing Artificial Skin IV: A Comparative Study on the Effect of Antibiotic and EGF on Cell Proliferation During Epidermal Healing" *Biomaterials* 22:2777-2783 (2001)).

It is believed that the stabilized cross-linked hydrogel of the present invention is useful as a wound healing device due to the intrinsic bioactivity of the material and the unique stereochemistry of the macromolecules in the presence of enhancing and strengthening polar amino acids. Several studies indicate the wound healing properties of collagen are attributable to its unique structure (see, Brass, L. F. and Bensusan, H., "The Role of Quaternary Structure in the Platelet-Collagen Interaction" *The Journal of Clinical Investigation* 54:1480-1487 (1974); Jaffe, R. and Dykin, D., "Evidence for a Structural Requirement for the Aggregation of Platelets by Collagen" *Journal of Clinical Investigation* 53:875-883 (1974); Postlewaithe, A. E. and Kang, A. H., "Collagen and Collagen Peptide Induced Chemotaxis of Human Blood Monocytes" *The Journal of Experimental Medicine* 143:1299-1307 (1976); and Reddi, A. H., "Collagen and Cell Differentiation" In: *Biochemistry of Collagen*, New York; Plenum Press, 449-477 (1976)). Similarly, the hydrogel of the present invention demonstrates a unique activity as a wound healing device because of the unique structure of the hydrogel matrix, which provides a scaffold for cells and attracts tissue building components and factors necessary to promote wound healing. The rapid mechanical integration of the crosslinked hydrogels with the wound bed, the similar mechanical properties of the material, and its ability to act as a preferred cell attachment scaffold material in the wound bed contribute to the usefulness of the matrix as a wound healing device.

In another aspect, the stabilized cross-linked hydrogel may be used as an adhesive (i.e., tissue sealant) in wound repair. The use of adhesives in wound repair is known in the art, and although such use has only recently gained FDA approval in the United States, wound repair adhesives have been used extensively in Canada and Europe for more than 20 years. Wound adhesives provide a popular alternative for wound closure over standard methods, such as sutures, staples, and adhesive strips, because they offer ease of use, decreased pain, reduced application time, and no follow-up for removal. The historically first wound adhesive made available, and the one still used most often today, is a type of cyanoacrylate, or common household superglue. Earlier wound adhesives were composed of N-butyl cyanoacrylate, but the preferred form today is 2-octyl cyanoacrylate. The use of cyanoacrylate wound adhesives, however, has several drawbacks that limit its use, such as, allergic reactions, presence of residual solvents, and migration of chemicals to other parts of the body. Further, cyanoacrylate adhesives should not be used in pregnant women or patients with a history of peripheral vascular disease, diabetes mellitus, or prolonged corticosteroid use, or on patients who have puncture wounds or bite or scratch wounds (animal or human in origin). Cyanoacrylate wound adhesives may only be used on the surface of the skin and on regularly shaped wounds with even surfaces that are easily pushed back together. This is necessary to insure none of the cyanoacrylate touches raw skin or enters the wound because it may cause severe irritation and can actually function to impair epithelialization within the wound.

There are newer alternatives to cyanoacrylate wound adhesives, but many of the alternatives possess additional drawbacks that complicate their widespread use. For example, adhesives composed of gelatin, resorcinol, and formaldehyde have been shown effective, but the toxicity and carcinogenic effects of formaldehyde limit their use.

Research has been performed indicating secretions from marine organisms, such as those used by barnacles to attach themselves to the hulls of ships, could be useful wound adhesives, but the detailed genetic engineering used to commercially produce the material has so far been found cost prohibitive. Biological glues, such as fibrin glue, or hemostatic agents are frequently used in cardiac or vascular surgeries to control diffuse bleeding. One example of such a hemostatic sealant, FloSeal® (FloSeal Matrix Hemostatic Sealant; Fusion Medical Technologies, Fremont, Calif.), is a combination of a cross-linked gelatin matrix and thrombin, which converts fibrinogen into fibrin monomers that polymerize to form a fibrin clot. None of these alternatives, however, offer a viable alternative to cyanoacrylates as an easily used wound adhesive that may be used in common practice.

The stabilized cross-linked hydrogel matrix of the present invention exhibits properties that make it useful as a wound adhesive while avoiding many of the drawbacks and contraindications associated with cyanoacrylates. The ability of the hydrogel to polymerize in situ has the effect of increasing cell-to-cell adhesion while simultaneously accelerating vascularization and promoting wound healing. The biocompatibility of the hydrogel allows for its use in a wide array of wounds, including situations where cyanoacrylates cannot be used, such as open wounds, wounds with jagged edges, and wounds around mucous membranes. In fact, the hydrogel of the present invention is most effective when introduced into the wound site as opposed to purely topical use. When the nascent hydrogel mixture is placed into the wound, the in situ polymerization of the hydrogel acts to begin a cascade of biological interactions that seal the wound and facilitate the healing process. The active binding sites on the gelatin and dextran macromolecules, in the presence of the added stabilizing and enhancing amino acids, not only cross-link with one another, but also form bonds to the native cells within the wound thereby forming a cross-linked hydrogel matrix that acts to pull the wound surfaces toward the central axis of the wound and hold the wound edges together. In addition to functioning to hold the wound edges together, the hydrogel further acts to form a water-insoluble barrier between the wound site and the exterior elements and acts as a cellular scaffold to encourage tissue regeneration at the site.

There are many embodiments in which the hydrogel could be packaged and delivered for use as a wound adhesive. For example, the reactive high molecular weight components could be packaged in a dual chamber apparatus that keeps the components separated during storage and enables the components to be simultaneously expelled into the wound where cross-linking could occur. Another contemplated embodiment involves packaging the components in an apparatus with degradable membranes separating the components Immediately prior to use, squeezing the apparatus would destroy the membranes allowing the components to mix providing a limited window of time for application to the wound so cross-linking could occur in situ. Various additional embodiments for packaging and delivery of the hydrogel for use as a wound adhesive would be readily apparent to one skilled in the art.

The bioactive cross-linked hydrogel matrix utilized in each of the embodiments described herein may be comprised solely of the two high molecular weight components cross-linked to one another. Preferably, each of the embodiments described herein may incorporate additional components such as the enhancing agents utilized in the preferred embodiments described above. Table 1 below lists preferred components present within the stabilized cross-linked hydrogel matrix of the present invention along with suitable concentrations as well as preferred concentrations for each component. Note that the concentrations listed in Table 1 for gelatin and dextran would also be suitable for alternative polyglycan and polypeptide components.

TABLE 1

| Component | Concentration Range | Preferred Concentration |
| --- | --- | --- |
| L-glutamic acid | 2 to 60 mM | 15 mM |
| L-lysine | 0.5 to 30 mM | 5.0 mM |
| Arginine | 1 to 40 mM | 10 mM |
| Gelatin | 0.01 to 40 mM | 2 mM |
| L-cysteine | 5 to 500 µM | 20 µM |
| EDTA | 0.01 to 10 mM | 4 mM |
| Dextran (oxidized & native forms) | 0.01 to 10 mM | 0.1 mM |

As noted above, the present invention provides numerous benefits including eliciting vascularization at a localized site, modulating localized wound healing response, and providing suitable means of developing a retrievable cell implantation device for cell-based therapeutics. Additional benefits may include the following: reduced scarring associated with degradation of bioerodible suture materials; improvement in the performance and long-term function of extravascular sensors such as glucose sensors routinely used for insulin delivery systems; improvement in the rate of healing, durability, and mechanical properties around structural implants such as artificial joints and tendons; reduced pain and associated complications arising from post surgical adhesions especially during abdominal or spinal injury; and improved integration between natural tissues and implanted structures (i.e. teeth, porous hydroxyapatite or ceramic materials for bone repair).

The cross-linked hydrogel matrix of the invention can be cross-linked outside the body and then implanted into a patient, or the hydrogel matrix can be allowed to cross-link in situ. While the hydrogel is stable at body temperatures, the actual cross-linking of the gelatin and dextran may also take place at body temperatures. This characteristic is particularly useful in view of the previously noted abilities of the cross-linked hydrogel to be used for tissue regeneration, vasculogenesis, as a bulking agent, and in other applications that would be readily apparent to one skilled in the art. Irregular tissue defects, such as those common in chemical, thermal, or trauma wounds, which require rapid healing, would also benefit from the ability to form in situ a bioactive hydrogel providing a cell attachment scaffold for tissue regeneration. An exemplary method for delivering the liquid components of the hydrogel to the desired site for in situ formation involves using a multi-chamber syringe. The multi-chamber syringe may be attached to a multi-lumen catheter or needle such that the high molecular weight components that form the cross-linked hydrogel do not interact until injected into the site inside the body where the matrix is needed. Another contemplated method involves the use of the multi-chamber syringe with a single lumen catheter or needle containing a static mixing element where the components remain separated until injection into the site, but the high molecular weight components actually contact one another within the lumen of the catheter or needle during injection into the specified site. Additional methods of delivery of the hydrogel components for in situ formation would be readily apparent to one skilled in the art. Typically, in the embodiments described above, one high molecular weight component, such as oxidized dextran, would be placed in one chamber of the syringe and the other high molecular weight component and additional enhancing agents would be placed in a separate chamber.

Experimental

The present invention is more fully illustrated by the following examples, which are set forth to illustrate the present invention and are not to be construed as limiting thereof. Unless otherwise indicated, all percentages refer to percentages by weight based on the total weight of the bioactive hydrogel matrix.

EXAMPLE 1

20 g of dextran (MW 500,000 Da) was weighed into a tared beaker containing 180 g phosphate-buffered saline. The dextran was dissolved, with constant stirring and 8 g sodium meta-periodate (available from Sigma, product number S1147) was added to the dissolved dextran. The beaker was wrapped in foil to prevent photo-catalyzed side-reactions, and placed in a refrigerator on a stirring plate for 12 hours at 5° C.±3° C. The beaker was removed, 50 mL ethylene glycol was added to consume excess periodate, and the quenching reaction was allowed to proceed for 30 minutes at room temperature. The reaction mixture was pH adjusted to 7.5±0.5 with 0.1 N NaOH. The reaction products were separated using tangential flow filtration (Filtron Mini-Ultrasette Pall Filtration Products, product number OS100077). The solution mass was reduced by half, and replaced with a 4-fold volume of phosphate buffered saline. The purified product was reduced to a final volume of 100 mL The final product was filter sterilized as a 20% dextran solution, and stored frozen until use. Hydroxylamine titration showed that this dextran was 20% oxidized.

A vial of a thermoreversible hydrogel matrix comprising gelatin and dextran and a vial of sterile filtered oxidized dextran were held at 39° C. for 30 minutes to melt the hydrogel and warm the oxidized dextran. An aliquot of 10 mL hydrogel was added to a 50 mL centrifuge tube, and rapidly mixed with 5 mL of oxidized dextran. The solution was cast into 100 mm culture plate, and gently swirled to form a uniform film across the bottom of the dish.

The reactive gel was allowed to cross-link at room temperature. The gel was washed with Medium 199, at 37° C. by flooding the surface of the gel with phenol red containing Medium 199. The Medium 199 overlay was replaced as required to maintain a neutral pH.

A tissue biopsy punch was used to produce 8 mm discs of cross-linked gel. Individual discs were placed in a 15 mL centrifuge tube containing 10 mL Medium 199 and were incubated at 37° C. for 2 weeks. Cross-linked gels were insoluble at 37° C. and retained their initial shape.

EXAMPLE 2

20 g of dextran (MW 500,000 Da) (available from Sigma, St. Louis, Mo.) was added to a tared beaker containing 200 mL of phosphate buffered saline (PBS) and stirred to form a uniform solution. A further 8 g of sodium meta-periodate was added to the dextran solution, which was wrapped in foil, and allowed to stir overnight at 5° C.±3° C. The reaction was quenched with 50 mL ethylene glycol, and the solution was adjusted with 0.1 M NaOH to a pH of 7.5±0.5. The product was purified using tangential filtration, and concentrated to a 20% dextran solution. Sterile filtered solutions were stored frozen until use. Hydroxylamine titration showed that this dextran was 18% oxidized. Frozen samples showed no loss in oxidation levels after 8 months storage at 20° C.±5° C.

A series of thermoreversible hydrogel and oxidized dextran formulations were prepared with fixed total gelatin concentration (12%) and increasing concentrations of oxidized dextran. As illustrated in FIG. 7, the strength of the cast gels increased as the concentration of oxidized dextran increased. Blends of fixed gelatin concentration and varying oxidized dextran concentration were tested for resistance to compression at two temperatures, 20° C. and 28° C. Gel strength increased with increasing oxidized dextran content and decreasing temperature.

EXAMPLE 3

20 g of dextran (MW 68,000 Da) (available from Sigma, St. Louis, Mo.) was added to a tared beaker containing 200 mL of phosphate buffered saline (PBS) and stirred to form a uniform solution. A further 8 g of sodium meta-periodate was added to the dextran solution, which was wrapped in foil, and allowed to stir overnight at 5° C.±3° C. The reaction was quenched with 50 mL ethylene glycol, and adjusted with 0.1 M NaOH to a pH of 7.5±0.5. The product was purified using tangential filtration, and concentrated to a 20% dextran solution. Sterile filtered solutions were stored frozen until use. Hydroxylamine titration showed that this dextran was 14% oxidized.

A thermoreversible hydrogel comprising gelatin and dextran was melted and added to several sets of mixtures of native and oxidized dextrans, mixed and cast into a T-25 culture flask. The concentration of oxidized dextran in each sample ranged from about 3% to about 21%.

The cast gels were allowed to cure at 5° C., ±3° C., overnight, and were washed extensively at 37° C. with phenol red containing Medium 199 (available from Sigma Chemical Company, St. Louis, Mo.) until the no further change in pH was evident colorimetrically. The material was rinsed extensively over four days with culture medium to neutralize residual acidic components.

Flasks containing 12% oxidized dextran were used for further cell culture studies. Normal neonatal human skin fibroblasts were provided in 6 mL of serum-containing culture medium and allowed to interact with the material over an additional two weeks at 37° C. After 24 hours, cells appeared to maintain normal health, showed attachment to the material by way of cytoplasmic processes, and also exhibited formation of multi-cell clusters. When observed 5 days later, one flask showed large cell aggregates that had formed in the culture and stellate cells in the lower layers of the culture where the large aggregates were attached to the cross-linked hydrogel material. Over the subsequent week, these aggregates continued to grow in size and appeared to contain healthy cells. Cultures were imaged at this time, and the resulting figures showed the appearance of the cell aggregates rising above the material surface with elongated processes and individual cells connecting the structure to the hydrogel substrate.

After approximately one month of exposure to the cross-linked material, cells were successfully dissociated from the hydrogel-containing flasks and replated onto standard tissue culture plastic surfaces, where they were observed to grow readily and showed a morphology similar to that of normally cultured fibroblasts.

EXAMPLE 4

A cross-linked hydrogel was prepared according to Example 1 above, wherein the hydrogel was comprised of 12% gelatin and 5% oxidized dextran (MW 500,000 Da). After manufacture, 5 ml of the cross-linked hydrogel was dispensed into a T-25 flask, to which was added 5 ml of culture medium (IMDM containing 10% FBS). The cross-linked hydrogel was solid at incubator temperature (37° C.). At 4 hours post-addition, the added medium had undergone a color change from red to light yellow, indicating a change in solution pH toward acidic. The initial 5 ml of culture medium was removed and a second 5 ml quantity was added to test the buffering capacity of the medium. Three days later, the same color change was observed. The culture medium was again removed and replaced with an additional 5 ml of culture medium. One day later, the there was minimal color change indicating neutralization of acidic leachables from the material. On the same day, a population of human skin fibroblasts (product number CCD-1112Sk, American Type Culture Collection) was dissociated and prepared for seeding into the flask. The cells were seeded in fresh medium at a 1:6 dilution in 6 mL total volume, and the flasks were returned to the incubator. After one hour, the cells were extending pseudopodia to connect with the cross-linked hydrogel, but were not yet well attached. After approximately 4 additional hours incubation, no additional attachment was observed. After one additional day, approximately 20% of the cells appeared to be forming aggregate-like structures, with aggregates ranging in size from about 2 to about 10 cells and attachment processes extending from the cells. The existing medium was poured off into a new T-25 flask and 3 mL of fresh medium was added to the culture.

The following day, the original and the replated cells were examined. Both cell populations appeared rounded and unhealthy, and the transplanted cells had not attached to the new flask surface.

Five days later (nine days from start of experiment), a third flask was examined, containing human skin fibroblasts, cross-linked hydrogel, and culture medium, which had been incubated undisturbed. This sample exhibited large aggregates. When checked again the following day, the aggregated cell clusters had grown in size and resembled embryo-like structures. Examination six days later revealed large multicellular structures on top of the cross-linked hydrogel with some cells apparently growing into the hydrogel at some sites.

EXAMPLE 5

1.5 mL of a 0.5 mg/mL solution of Bis-[β-(4-azidosalicy-lamido)ethyl]disulfide (BASED), a crosslinking agent, in dimethyl sulfoxide (DMSO), is added to a foil-wrapped vessel containing 15 mL of liquid thermoreversible hydrogel containing gelatin and dextran. Photoactivated non-specific cross-linking of the thermoreversible hydrogel occurs upon exposure of the reactive mixture to long-wavelength light, such as that provided by continuous exposure to a 550-watt bulb (flood light used in photography). Longer exposure times demonstrated better cross-linking.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A method of performing bone repair or reconstruction, the method comprising administering a bone implant material to a bone defect site, wherein the bone implant material is a combination of: a crosslinked bioactive hydrogel matrix comprising a polyglycan crosslinked to a polypeptide; at least one enhancing agent selected from the group consisting of polar amino acids, intact collagen, divalent cation chelators, and combinations thereof; and an osteoinductive or osteoconductive material comprising hydroxyapatite;
   wherein the polyglycan is a polysaccharide or a sulfated polysaccharide, and the tissue-derived polypeptide is selected from the group consisting of collagens, gelatins, keratin, decorin, aggrecan, glycoproteins, laminin, nidogen, fibulin, and fibrillin.

2. The method of claim 1, further comprising, prior to said administering step, forming the bone implant material into a paste and casting the paste into a desired shape.

3. The method of claim 1, wherein the polyglycan is selected from the group consisting of glycosaminoglycans, glucosaminoglycans, dextran, heparan, heparin, hyaluronic acid, alginate, agarose, carageenan, amylopectin, amylose, glycogen, starch, cellulose, chitin, heparan sulfate, chondroitin sulfate, dextran sulfate, dermatan sulfate, and keratan sulfate.

4. The method of claim 1, wherein the polyglycan has a molecular weight of about 2,000 to about 8,000,000 Da.

5. The method of claim 1, wherein the polypeptide has a molecular weight of about 3,000 to about 3,000,000 Da.

6. The method of claim 1, wherein the polyglycan is dextran and the polypeptide is gelatin.

7. The method of claim 1, wherein the at least one enhancing agent comprises at least one polar amino acid selected from the group consisting of tyrosine, cysteine, serine, threonine, asparagine, glutamine, aspartic acid, glutamic acid, arginine, lysine, histidine, and mixtures thereof.

8. The method of claim 1, wherein the at least one enhancing agent comprises ethylenediaminetetraacetic acid or a salt thereof.

* * * * *

UNITED STATES PATENT AND TRADEMARK OFFICE
CERTIFICATE OF CORRECTION

PATENT NO. : 9,623,146 B2
APPLICATION NO. : 14/610487
DATED : April 18, 2017
INVENTOR(S) : Francis Vincent Lamberti, Richard Chris Klann and Ronald Stewart Hill Page 1 of 1

It is certified that error appears in the above-identified patent and that said Letters Patent is hereby corrected as shown below:

On the Title Page

(73) Assignee is listed as RTI Surgical Technology, Inc. Please amend the Assignee to Pioneer Surgical Technology, Inc.,.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*